US011904013B2

(12) United States Patent
Leng et al.

(10) Patent No.: US 11,904,013 B2
(45) Date of Patent: Feb. 20, 2024

(54) IMMUNOGENIC COMPOSITION AND USE THEREOF

(71) Applicant: ADIMMUNE CORPORATION, Taichung (TW)

(72) Inventors: Chih-Hsiang Leng, Taichung (TW); Po-Hsu Su, Taichung (TW); Po-Kang Chen, Taichung (TW)

(73) Assignee: ADIMMUNE CORPORATION, Taichung (TW)

( * ) Notice: Subject to any disclaimer, the term of this patent is extended or adjusted under 35 U.S.C. 154(b) by 252 days.

(21) Appl. No.: 17/246,740

(22) Filed: May 3, 2021

(65) Prior Publication Data

US 2021/0353742 A1 Nov. 18, 2021

Related U.S. Application Data

(60) Provisional application No. 63/019,442, filed on May 4, 2020.

(51) Int. Cl.

| | |
|---|---|
| ***A61K 39/215*** | (2006.01) |
| ***C12N 15/86*** | (2006.01) |
| ***C07K 14/005*** | (2006.01) |
| ***A61P 31/14*** | (2006.01) |
| ***C07K 7/08*** | (2006.01) |
| ***C12N 7/00*** | (2006.01) |

(52) U.S. Cl.

CPC .............. *A61K 39/215* (2013.01); *C07K 7/08* (2013.01); *C12N 7/00* (2013.01); *C07K 2319/02* (2013.01); *C07K 2319/30* (2013.01); *C12N 2710/14043* (2013.01); *C12N 2770/20034* (2013.01)

(58) Field of Classification Search

CPC .............. A61K 39/215; A61K 2039/53; A61K 2039/6056; A61K 39/12; A61K 2039/5256; C12N 7/00; C12N 2710/14043; C12N 2770/20034; C12N 2710/14143; C12N 2770/20022; C12N 15/86; C07K 2319/02; A61P 31/14

See application file for complete search history.

(56) References Cited

FOREIGN PATENT DOCUMENTS

WO WO-2021195089 A1 * 9/2021

OTHER PUBLICATIONS

Padron-Regalado E. Vaccines for SARS-CoV-2: Lessons from Other Coronavirus Strains. Infect Dis Ther. Jun. 2020;9(2):255-274. doi: 10.1007/s40121-020-00300-x. Epub Apr. 23, 2020. (Year: 2020).*

A Guide to Polyacrylamide Gel Electrophoresis and Detection, Bio-Rad Laboratories, Inc., bulletin 6040 ver C.

Samuel Karlin et al., Applications and statistics for multiple high-scoring segments in molecular sequences, Proc. Natl. Acad. Sci USA, vol. 90, pp. 5873-5877, Jun. 1993.

An efficient site-specific transposition system to generate baculovirus for high-level expression of recombinant proteins, Bac-to-Bac™ Baculovirus Expression System User Guide, Catalog Nos. 10359-016, 10360-014, 10584-027,10712-024, Publication No. MAN0000414, Thermo Fisher Scientific, Jul. 16, 2018.

Stephen F. Altschul et al., Basic Local Alignment Search Tool, J. Mol. Biol. (1990) 215, 403-110.

Stephen F. Altschul et al., Gapped BLAST and PSI-BLAST: a new generation of protein database search programs,Nucleic Acids Research, 1997, vol. 25, No. 17 3389-3402, Oxford University Press.

Samuel Karlin et al., Methods for assessing the statistical significance of molecular sequence features by using general scoring schemes, Proc. Natl. Acad Sci. USA, vol. 87, pp. 2264-2268, Mar. 1990.

* cited by examiner

*Primary Examiner* — Janet L Andres
*Assistant Examiner* — Ruixue Wang

(57) ABSTRACT

An immunogenic composition, a SARS-CoV-2 vaccine and a vector are introduced. The immunogenic composition has a recombinant protein having a sequence selected from the group consisting of SEQ ID NO: 1, SEQ ID NO: 2, SEQ ID NO: 3, SEQ ID NO: 4, and any polypeptide encoded by a polynucleotide which is at least 80% homologous with SEQ ID NO: 1-4, wherein the recombinant protein contains an IgG1 Fc protein fragment having a length of at least 6 amino acids; or a nucleic acid molecule encoding the recombinant protein. The SARS-CoV-2 vaccine has the above recombinant protein or the nucleic acid molecule encoding the above recombinant protein. The vector has the nucleic acid molecule encoding the above recombinant protein.

15 Claims, 19 Drawing Sheets

Specification includes a Sequence Listing.

NITNLCPFGEVFNATRFASVYAWNRKRISNCVADYSVLYNSASFSTFKCYGVSP
TKLNDLCFTNVYADSFVIRGDEVRQIAPGQTGKIADYNYKLPDDFTGCVIAW
NSNNLDSKVGGNYNYLYRLFRKSNLKPFERDISTEIYQAGSTPCNGVEGFNCY
FPLQSYGFQPTNGVGYQPYRVVVLSFELLHAPATVCGPKKSTNLVKNKCVNF
NFNGLTGTGGGSGGSGGSGGSGGSTCPPCPAPELLGGPSVFLFPPKPKDTLMIS
RTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLT
VDKSRWQQGNVFSCSVMHEALHNHYTQKSLSLSPGK

FIG.1

MSLGAENSVAYSNNSIAIPTNFTISVTTEILPVSMTKTSVDCTMYICGDSTECSN
LLLQYGSFCTQLNRALTGIAVEQDKNTQEVFAQVKQIYKTPPIKDFGGFNFSQI
LPDPSKPSKRSFIEDLLFNKVTLADAGFIKQYGDCLGDIAARDLICAQKFNGLT
VLPPLLTDEMIAQYTSALLAGTITSGWTFGAGAALQIPFAMQMAYRFNGIGVT
QNVLYENQKLIANQFNSAIGKIQDSLSSTASALGKLQDVVNQNAQALNTLVK
QLSSNFGAISSVLNDILSRLDKVEAEVQIDRLITGRLQSLQTYVTQQLIRAAEIR
ASANLAATKMSECVLGQSKRVDFCGKGYHLMSFPQSAPHGVVFLHVTYVPA
QEKNFTTAPAICHDGKAHFPREGVFVSNGTHWFVTQRNFYEPQIITTDNTFVS
GNCDVVIGIVNNTVYDPLQPELDSFKEELDKYFKNHTSPDVDLGDISGINASV
VNIQKEIDRLNEVAKNLNESLIDLQELGKYEQYIKWPGGSGGSGGSGGSGGST
CPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNH
YTQKSLSLSPGK

FIG.2

VNLTTRTQLPPAYTNSFTRGVYYPDKVFRSSVLHSTQDLFLPFFSNVTWFHAIH
VSGTNGTKRFDNPVLPFNDGVYFASTEKSNIIRGWIFGTTLDSKTQSLLIVNNA
TNVVIKVCEFQFCNDPFLGVYYHKNNKSWMESEFRVYSSANNCTFEYVSQPF
LMDLEGKQGNFKNLREFVFKNIDGYFKIYSKHTPINLVRDLPQGFSALEPLVD
LPIGINITRFQTLLALHRSYLTPGDSSSGWTAGAAAYYVGYLQPRTFLLKYNEN
GTITDAVDCALDPLSETKCTLKSFTVEKGIYQTSNFRVQPTESIVRFPNITNLCP
FGEVFNATRFASVYAWNRKRISNCVADYSVLYNSASFSTFKCYGVSPTKLNDL
CFTNVYADSFVIRGDEVRQIAPGQTGKIADYNYKLPDDFTGCVIAWNSNNLDS
KVGGNYNYLYRLFRKSNLKPFERDISTEIYQAGSTPCNGVEGFNCYFPLQSYG
FQPTNGVGYQPYRVVVLSFELLHAPATVCGPKKSTNLVKNKCVNFNFNGLTG
TGVLTESNKKFLPFQQFGRDIADTTDAVRDPQTLEILDITPCSFGGVSVITPGTN
TSNQVAVLYQDVNCTEVPVAIHADQLTPTWRVYSTGSNVFQTRAGCLIGAEH
VNNSYECDIPIGAGICASYQTQTNSPRRARGGSGGSGGSGGSGGSTCPPCPAPE
LLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSL
SLSPGK

FIG.3

VNLTTRTQLPPAYTNSFTRGVYYPDKVFRSSVLHSTQDLFLPFFSNVTWFHAIH
VSGTNGTKRFDNPVLPFNDGVYFASTEKSNIIRGWIFGTTLDSKTQSLLIVNNA
TNVVIKVCEFQFCNDPFLGVYYHKNNKSWMESEFRVYSSANNCTFEYVSQPF
LMDLEGKQGNFKNLREFVFKNIDGYFKIYSKHTPINLVRDLPQGFSALEPLVD
LPIGINITRFQTLLALHRSYLTPGDSSSGWTAGAAAYYVGYLQPRTFLLKYNEN
GTITDAVDCALDPLSETKCTLKSFTVEKGIYQTSNFRVQPTESIVRFPNITNLCP
FGEVFNATRFASVYAWNRKRISNCVADYSVLYNSASFSTFKCYGVSPTKLNDL
CFTNVYADSFVIRGDEVRQIAPGQTGKIADYNYKLPDDFTGCVIAWNSNNLDS
KVGGNYNYLYRLFRKSNLKPFERDISTEIYQAGSTPCNGVEGFNCYFPLQSYG
FQPTNGVGYQPYRVVVLSFELLHAPATVCGPKKSTNLVKNKCVNFNFNGLTG
TGVLTESNKKFLPFQQFGRDIADTTDAVRDPQTLEILDITPCSFGGVSVITPGTN
TSNQVAVLYQDVNCTEVPVAIHADQLTPTWRVYSTGSNVFQTRAGCLIGAEH
VNNSYECDIPIGAGICASYQTQTNSPRRARSVASQSIIAYTMSLGAENSVAYSN
NSIAIPTNFTISVTTEILPVSMTKTSVDCTMYICGDSTECSNLLLQYGSFCTQLN
RALTGIAVEQDKNTQEVFAQVKQIYKTPPIKDFGGFNFSQILPDPSKPSKRSFIE
DLLFNKVTLADAGFIKQYGDCLGDIAARDLICAQKFNGLTVLPPLLTDEMIAQ
YTSALLAGTITSGWTFGAGAALQIPFAMQMAYRFNGIGVTQNVLYENQKLIA
NQFNSAIGKIQDSLSSTASALGKLQDVVNQNAQALNTLVKQLSSNFGAISSVL
NDILSRLDKVEAEVQIDRLITGRLQSLQTYVTQQLIRAAEIRASANLAATKMSE
CVLGQSKRVDFCGKGYHLMSFPQSAPHGVVFLHVTYVPAQEKNFTTAPAICH
DGKAHFPREGVFVSNGTHWFVTQRNFYEPQIITTDNTFVSGNCDVVIGIVNNT
VYDPLQPELDSFKEELDKYFKNHTSPDVDLGDISGINASVVNIQKEIDRLNEVA
KNLNESLIDLQELGKYEQYIKWPGGSGGSGGSGGSGGSTCPPCPAPELLGGPS
VFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK

FIG.4

MLLVNQSHQGFNKEHTSKMVSAIVLYVLLAAAAHSAFAAD

N protein
MSDNGPQNQRNAPRITFGGPSDSTGSNQNGERSGARSKQRRPQGLPNNTASW
FTALTQHGKEDLKFPRGQGVPINTNSSPDDQIGYYRRATRRIRGGDGKMKDLS
PRWYFYYLGTGPEAGLPYGANKDGIIWVATEGALNTPKDHIGTRNPANNAAI
VLQLPQGTTLPKGFYAEGSRGGSQASSRSSSRSRNSSRNSTPGSSRGTSPARMA
GNGGDAALALLLLDRLNQLESKMSGKGQQQQGQTVTKKSAAEASKKPRQK
RTATKAYNVTQAFGRRGPEQTQGNFGDQELIRQGTDYKHWPQIAQFAPSASA
FFGMSRIGMEVTPSGTWLTYTGAIKLDDKDPNFKDQVILLNKHIDAYKTFPPT
EPKKDKKKKADETQALPQRQKKQQTVTLLPAADLDDFSKQLQQSMSSADST
QA E protein
MYSFVSEETGTLIVNSVLLFLAFVVFLLVTLAILTALRLCAYCCNIVNVSLVKPS
FYVYSRVKNLNSSRVPDLLV M protein
MADSNGTITVEELKKLLEQWNLVIGFLFLTWICLLQFAYANRNRFLYIIKLIFLW
LLWPVTLACFVLAAVYRINWITGGIAIAMACLVGLMWLSYFIASFRLFARTRS
MWSFNPETNILLNVPLHGTILTRPLLESELVIGAVILRGHLRIAGHHLGRCDIKD
LPKEITVATSRTLSYYKLGASQRVAGDSGFAAYSRYRIGNYKLNTDHSSSSDNI
ALLVQ

FIG.12

AAAATTTTTACTGTTTTCGTAACAGTTTTGTAATAAAAAAACCTATAAATATT
CCGGATTATTCATACCGTCCCACCATCGGGCGCGGATCCCGGTCCGAAGCG
CGCGGAATTCATGCTGCTGGTCAACCAGAGCCACCAGGGTTTCAACAAGG
AACACACCTCAAAGATGGTGTCCGCCATCGTGCTGTACGTCCTGCTGGCTG
CTGCTGCTCACTCAGCTTTCGCTGCCGACAACATCACCAACCTGTGCCCAT
TCGGCGAGGTCTTCAACGCTACTAGGTTCGCCTCCGTGTACGCTTGGAACC
GCAAGCGTATCAGCAACTGCGTGGCCGACTACTCTGTCCTGTACAACTCCG
CTAGCTTCTCTACTTTCAAGTGCTACGGAGTGTCACCTACCAAGCTGAACG
ACCTGTGCTTCACTAACGTGTACGCCGACTCCTTCGTCATCCGCGGTGACG
AAGTGCGTCAGATCGCCCCAGGACAGACCGGCAAGATCGCTGACTACAAC
TACAAGCTGCCTGACGACTTCACTGGATGCGTCATCGCTTGGAACAGCAAC
AACCTGGACTCTAAAGTGGGTGGCAACTACAACTACCTGTACAGGCTGTTC
AGAAAGAGCAACCTGAAGCCTTTCGAGAGGGACATCAGCACCGAAATCTA
CCAGGCCGGTTCTACTCCCTGCAACGGCGTCGAAGGATTCAACTGCTACTT
CCCCCTGCAGTCTTACGGCTTCCAGCCAACCAACGGTGTGGGCTACCAGCC
TTACAGAGTGGTCGTGCTGAGCTTCGAACTCCTCCACGCTCCAGCTACTGT
CTGCGGTCCTAAGAAGTCTACTAACCTGGTGAAGAACAAGTGCGTCAACTT
CAACTTCAACGGTCTGACTGGAACTGGAGGTGGCTCCGGAGGTAGCGGCG
GATCTGGTGGCTCAGGAGGTTCTACTTGCCCTCCCTGCCCAGCTCCTGAGC
TGCTGGGCGGACCCTCCGTGTTCCTGTTCCCACCTAAGCCAAAGGACACTC
TGATGATCTCACGCACCCCCGAAGTCACTTGCGTCGTGGTCGACGTGTCCC
ACGAGGACCCAGAAGTCAAGTTCAACTGGTACGTGGACGGCGTGGAGGTC
CACAACGCTAAGACCAAGCCCAGGGAGGAACAGTACAACTCAACCTACAG
AGTGGTCTCCGTGCTGACTGTCCTGCACCAGGACTGGCTGAACGGCAAGG
AGTACAAGTGCAAGGTCAGCAACAAGGCTCTGCCCGCCCCAATCGAGAAG
ACCATCTCTAAGGCCAAGGGACAGCCTCGCGAACCCCAGGTGTACACTCT
GCCCCCAAGCCGTGAGGAAATGACCAAGAACCAGGTCTCTCTGACTTGCC
TGGTGAAGGGATTCTACCCTTCAGACATCGCTGTGGAGTGGGAATCCAACG
GTCAGCCCGAAAACAACTACAAGACCACTCCTCCCGTCCTGGACAGCGAC
GGCTCTTTCTTCCTGTACTCAAAGCTGACCGTGGACAAGTCCCGTTGGCAG
CAGGGAAACGTGTTCTCATGCTCCGTCATGCACGAGGCTCTGCACAACCAC
TACACTCAGAAGAGCCTGTCTCTGTCACCTGGCAAGTAACTCGAGGCATGC
GGTACCAAGCTTGTCGAGAAGTACTAGAGGATCATAATCAGCCATACCACA
TTTGTAGAGGTTTTACTTGCTTTAAAAAACCTCCCACACCTCCCCCTGAACC
TGAAACATAAAATGAATGCAATTGTTGTTGTTAACTTGTTTATTGCAGCTTAT
AATGGTTACAAATAAAGCAATAGCATCACAAATTTCACAAATAAAGCATTTT
TTTCACTGCATCTAGTGTATTGTCAAACTCATCATGTATCTATCATGTCTGAT

FIG.13

CTGATCACTGCCTTGAGCTTAGAGATCCGACCGATATGGATCTAAGTCCACT
ATTTGTCATTTTACTTCGGATAGCTACGAACGCTACACCAGCTGCA

FIG.13 continued

AAGATTTACTGTTTTCGTAACAGTTTTGTAATAAAAAAACCTATAAATATTCC
GGATTATTCATACCGTCCCACCATCGGGCGCGGATCCCGGTCCGAAGCGCG
CGGAATTCATGCTGCTGGTGAACCAGTCACACCAGGGCTTCAACAAGGAG
CACACCTCAAAGATGGTCTCCGCTATCGTCCTGTACGTGCTGCTGGCTGCT
GCTGCTCACTCCGCCTTCGCTGCCGACATGAGCCTGGGAGCTGAGAACTCT
GTGGCCTACTCAAACAACTCCATCGCCATCCCCACCAACTTCACTATCAGC
GTCACCACTGAAATCCTGCCAGTGAGCATGACCAAGACTTCTGTCGACTGC
ACCATGTACATCTGCGGAGACAGCACTGAGTGCTCTAACCTGCTGCTGCAG
TACGGTTCTTTCTGCACCCAGCTGAACCGCGCTCTGACTGGCATCGCCGTG
GAGCAGGACAAGAACACCCAGGAAGTCTTCGCTCAGGTGAAGCAGATCTA
CAAGACTCCTCCCATCAAGGACTTCGGTGGCTTCAACTTCTCCCAGATCCT
GCCTGACCCCAGCAAGCCATCTAAGAGGTCATTCATCGAGGACCTGCTGTT
CAACAAGGTGACCCTGGCTGACGCCGGCTTCATCAAGCAGTACGGAGACT
GCCTGGGTGACATCGCTGCCAGAGACCTGATCTGCGCTCAGAAGTTCAAC
GGACTGACCGTCCTGCCACCTCTGCTGACTGACGAAATGATCGCTCAGTAC
ACCTCTGCTCTGCTGGCTGGTACCATCACTTCTGGCTGGACTTTCGGAGCT
GGTGCTGCCCTGCAGATCCCTTTCGCTATGCAGATGGCCTACCGTTTCAACG
GCATCGGAGTCACTCAGAACGTGCTGTACGAGAACCAGAAGCTGATCGCT
AACCAGTTCAACAGCGCCATCGGAAAGATCCAGGACTCACTGTCCAGCAC
TGCTTCTGCTCTGGGCAAGCTGCAGGACGTGGTCAACCAGAACGCTCAGG
CCCTGAACACTCTGGTGAAGCAACTGTCTTCAAACTTCGGAGCTATCTCCA
GCGTCCTGAACGACATCCTGTCCCGCCTGGACAAGGTCGAGGCCGAAGTG
CAGATCGACCGCCTGATCACCGGTCGTCTGCAGTCACTGCAGACCTACGTG
ACTCAGCAGCTGATCAGGGCTGCCGAGATCAGAGCTTCCGCCAACCTGGC
TGCCACTAAGATGTCAGAATGCGTGCTGGGACAGTCCAAGCGTGTCGACTT
CTGCGGCAAGGGCTACCACCTGATGTCATTCCCCCAGTCCGCTCCACACGG
TGTGGTCTTCCTGCACGTCACCTACGTGCCAGCCCAGGAAAAGAACTTCAC
CACTGCTCCTGCCATCTGCCACGACGGCAAGGCTCACTTCCCCCGCGAGG
GAGTCTTCGTGAGCAACGGTACCCACTGGTTCGTGACTCAGCGTAACTTCT
ACGAACCACAGATCATCACCACTGACAACACCTTCGTCTCTGGCAACTGCG
ACGTGGTCATCGGAATCGTCAACAACACTGTGTACGACCCTCTGCAGCCCG
AGCTGGACAGCTTCAAGGAGGAACTGGACAAGTACTTCAAGAACCACACC
TCTCCTGACGTGGACCTGGGCGACATCTCAGGAATCAACGCTTCCGTGGTC

FIG.14

AACATCCAGAAGGAGATCGACAGGCTGAACGAAGTCGCCAAGAACCTGA
ACGAATCACTGATCGACCTGCAGGAGCTGGGCAAGTACGAACAGTACATC
AAGTGGCCCGGAGGTTCCGGCGGAAGCGGTGGCTCTGGAGGTTCAGGCG
GATCCACCTGCCCTCCTTGCCCAGCTCCTGAACTGCTGGGTGGCCCTTCCG
TGTTCCTGTTCCCTCCCAAGCCCAAGGACACTCTGATGATCAGCAGAACCC
CAGAAGTGACTTGCGTGGTCGTGGACGTCTCTCACGAGGACCCTGAAGTC
AAGTTCAACTGGTACGTGGACGGCGTCGAAGTGCACAACGCTAAGACCAA
GCCCCGCGAGGAACAGTACAACAGCACCTACCGTGTCGTGTCTGTCCTGA
CTGTGCTGCACCAGGACTGGCTGAACGGCAAGGAGTACAAGTGCAAGGTG
TCAAACAAGGCTCTGCCCGCCCCAATCGAGAAGACCATCTCCAAGGCCAA
GGGCCAGCCAAGGGAACCTCAGGTCTACACTCTGCCACCTTCAAGAGAGG
AAATGACCAAGAACCAGGTCTCCCTGACTTGCCTGGTGAAGGGCTTCTACC
CTTCAGACATCGCTGTGGAGTGGGAATCCAACGGACAGCCCGAGAACAAC
TACAAGACCACTCCCCCAGTGCTGGACAGCGACGGTTCTTTCTTCCTGTAC
AGCAAGCTGACCGTCGACAAGTCTAGGTGGCAGCAGGGCAACGTCTTCTC
TTGCTCAGTGATGCACGAAGCTCTGCACAACCACTACACTCAGAAGTCCCT
GAGCCTGTCTCCTGGCAAGTAACTCGAGGCATGCGGTACCAAGCTTGTCGA
GAAGTACTAGAGGATCATAATCAGCCATACCACATTTGTAGAGGTTTTACTT
GCTTTAAAAACCTCCCACACCTCCCCTGAACCTGAAACATAAATGATGCAT
GTGTGGTACTGTATGCAGCTATATGTACATTAGCATAGCATCACAATTCACAA
TAAGGCATTTTTCCATGCATTCCAGTGTGATGGTCCAGCTCATCATGTACTAT
CAGTTGATCAGATCATGCTGACCTAGAATCCGAACCGATAGTGATC

FIG. 14 continued

AAGAAATTTACTGTTTTCGTAACAGTTTTGTAATAAAAAAACCTATAAATAT
TCCGGATTATTCATACCGTCCCACCATCGGGCGCGGATCCCGGTCCGAAGC
GCGCGGAATTCATGCTGCTGGTCAACCAGAGCCACCAGGGATTCAACAAG
GAGCACACTTCCAAGATGGTGAGCGCTATCGTGCTGTACGTCCTGCTCGCT
GCTGCTGCTCACTCTGCTTTCGCTGCTGACGTCAACCTCACCACTAGGACC
CAGCTGCCTCCCGCTTACACCAACTCATTCACTAGGGGTGTGTACTACCCT
GACAAGGTGTTCAGATCCAGCGTCCTGCACTCCACTCAGGACCTGTTCCTG
CCCTTCTTCAGCAACGTCACCTGGTTCCACGCTATCCACGTGTCCGGCACC
AACGGAACTAAGAGGTTCGACAACCCAGTCCTGCCTTTCAACGACGGCGT
GTACTTCGCCTCTACCGAGAAGTCAAACATCATCAGAGGTTGGATCTTCGG
CACCACTCTGGACTCCAAGACTCAGAGCCTGCTGATCGTCAACAACGCTAC
CAACGTGGTCATCAAGGTGTGCGAGTTCCAGTTCTGCAACGACCCTTTCCT
GGGAGTCTACTACCACAAGAACAACAAGTCTTGGATGGAGTCAGAGTTCC
GCGTCTACTCTTCAGCCAACAACTGCACTTTCGAGTACGTGTCTCAGCCCT
TCCTGATGGACCTGGAAGGCAAGCAGGGCAACTTCAAGAACCTGCGCGAG
TTCGTGTTCAAGAACATCGACGGTTACTTCAAGATCTACTCCAAGCACACC
CCTATCAACCTGGTCCGTGACCTGCCCCAGGGTTTCAGCGCTCTGGAGCCT
CTGGTGGACCTGCCCATCGGCATCAACATCACCCGCTTCCAGACTCTGCTG
GCTCTGCACCGTTCCTACCTGACTCCAGGCGACTCCAGCTCTGGATGGACT
GCTGGTGCTGCTGCTTACTACGTGGGCTACCTGCAGCCTAGGACCTTCCTG
CTGAAGTACAACGAAAACGGAACCATCACAGACGCTGTGGACTGCGCTCT
GGACCCACTGTCCGAAACCAAGTGCACTCTGAAGAGCTTCACCGTGGAGA
AGGGCATCTACCAGACTTCTAACTTCAGGGTCCAGCCAACCGAATCAATCG
TGAGATTCCCCAACATCACTAACCTGTGCCCATTCGGAGAGGTCTTCAACG
CCACCCGTTTCGCTTCCGTGTACGCCTGGAACAGGAAGAGAATCTCTAACT
GCGTGGCTGACTACTCAGTCCTGTACAACTCAGCCTCCTTCAGCACCTTCA
AGTGCTACGGTGTGTCTCCTACTAAGCTGAACGACCTGTGCTTCACCAACG
TGTACGCTGACTCATTCGTCATCAGGGGCGACGAGGTGAGACAGATCGCTC
CCGGACAGACTGGCAAGATCGCCGACTACAACTACAAGCTGCCAGACGAC
TTCACCGGTTGCGTCATCGCCTGGAACTCCAACAACCTGGACAGCAAAGT
GGGTGGCAACTACAACTACCTGTACCGCCTGTTCCGTAAGTCCAACCTGAA
GCCATTCGAGAGGGACATCTCTACTGAAATCTACCAGGCTGGCTCAACCCC
TTGCAACGGCGTCGAGGGATTCAACTGCTACTTCCCACTGCAGAGCTACGG
ATTCCAGCCTACTAACGGCGTGGGATACCAGCCCTACAGAGTGGTCGTGCT
GTCCTTCGAACTGCTGCACGCCCCAGCTACTGTGTGCGGACCTAAGAAGA

FIG.15

GCACCAACCTGGTGAAGAACAAGTGCGTCAACTTCAACTTCAACGGTCTG
ACCGGTACTGGCGTCCTGACCGAGTCTAACAAGAAGTTCCTGCCATTCCAG
CAGTTCGGTCGCGACATCGCTGACACTACCGACGCCGTGCGTGACCCACA
GACCCTGGAAATCCTGGACATCACTCCATGCTCTTTCGGAGGTGTGTCAGT
CATCACTCCTGGCACCAACACTTCAAACCAGGTGGCCGTCCTGTACCAGGA
CGTCAACTGCACCGAGGTGCCTGTCGCCATCCACGCTGACCAGCTGACCC
CCACTTGGCGCGTCTACTCAACCGGTTCCAACGTGTTCCAGACTCGTGCTG
GCTGCCTGATCGGAGCCGAGCACGTGAACAACTCCTACGAATGCGACATCC
CCATCGGAGCTGGTATCTGCGCCTCCTACCAGACCCAAACTAACAGCCCAC
GCAGGGCTCGCGGCGGAAGCGGTGGCTCTGGAGGTTCAGGCGGATCCGGT
GGCAGCACTTGCCCACCTTGCCCAGCTCCAGAACTGCTGGGAGGTCCAAG
CGTGTTCCTGTTCCCTCCTAAGCCTAAGGACACCCTGATGATCTCCCGTACC
CCTGAGGTCACTTGCGTCGTGGTCGACGTGAGCCACGAGGACCCCGAAGT
CAAGTTCAACTGGTACGTGGACGGCGTGGAAGTCCACAACGCTAAGACCA
AGCCCCGCGAGGAACAGTACAACTCCACTTACCGTGTGGTCAGCGTGCTG
ACCGTCCTGCACCAGGACTGGCTGAACGGAAAGGAATACAAGTGCAAGGT
CTCTAACAAGGCCCTGCCTGCTCCCATCGAAAAGACTATCTCAAAGGCTAA
GGGTCAGCCCAGGGAGCCACAGGTGTACACCCTGCCTCCCTCTAGAGAGG
AAATGACCAAGAACCAGGTCTCACTGACTTGCCTGGTGAAGGGATTCTACC
CATCCGACATCGCCGTGGAGTGGGAAAGCAACGGTCAGCCTGAGAACAAC
TACAAGACCACTCCACCTGTCCTGGACTCTGACGGTTCATTCTTCCTGTACT
CTAAGCTGACTGTGGACAAGTCACGTTGGCAGCAGGGCAACGTGTTCTCT
TGCTCAGTCATGCACGAAGCTCTGCACAACCACTACACCCAGAAGTCCCTG
AGCCTGTCTCCTGGCAAGTAACTCGAGGCATGCGGTACCAAGCTTGTCGAG
AAGTACTAGAGGATCATAATCAGCCATACCACATTTGTAGAGGTTTTACTTG
CTTTAAAAAACCTCCCACACCTCCCCCTGAACCTGAAACATAAAATGAATG
CAATTGTTGTTGTTAACTTGTTTATTGCAGCTTATAATGGTTACAAATAAAGC
AATAGCATCACAAATTTCACAAATAAAGCATTTTTTTCACTGCATTCTAGTT
GTGGTTTGTCCAAACTCATCAATGTATCTTATCATGTCTGGATCTGATCACTG
CTTGAGCCTAGGAGATCCGAACCAGATAAGTGAAATCTAGTTCCAAACTAT
TTTGTCATTTTTAATTTTCGTATTAGCTTACGACGCTACACCCAGTACCCATC
TATTTTGTCACTCTTCCCTAAATAATCCTTAAAAACTCCATTTCCACCCCTCC
CAGTTCCCAACTAATTTTGTCCGCCCACACAGGGGCATTTTTCTTCCTGTTA
TGTGAATTCCTGCAGCCCGGGAGGATCCACTAAGTTCTAGAGCGGCCGCCA
CGCGGTGGAGCTCCGGCTTTTGTTGCCGGTTACTGGAGGGTCAGTTGCGCG
CTTAGACGTATCATGGGTCGTAGCTGTTATCGCTGGCGTGCACCTGCACGA
GCTATGAGGAGGAGGAGACTTA

FIG.15 continued

AAGAATTTTACTGTTTTCGTAACAGTTTTGTAATAAAAAAACCTATAAATATT
CCGGATTATTCATACCGTCCCACCATCGGGCGCGGATCCCGGTCCGAAGCG
CGCGGAATTCATGCTGCTGGTGAACCAGTCCCACCAGGGATTCAACAAGG
AGCACACTAGCAAGATGGTCTCTGCTATCGTGCTGTACGTCCTGCTGGCTG
CTGCTGCTCACAGCGCCTTCGCTGCCGACGTGAACCTCACCACTAGGACCC
AGCTGCCTCCCGCTTACACCAACTCTTTCACTAGGGGTGTCTACTACCCAG
ACAAGGTGTTCAGATCCAGCGTCCTGCACAGCACTCAGGACCTGTTCCTGC
CTTTCTTCTCTAACGTGACCTGGTTCCACGCCATCCACGTCTCCGGTACCAA
CGGCACTAAGCGCTTCGACAACCCAGTCCTGCCTTTCAACGACGGCGTGTA
CTTCGCTTCAACCGAAAAGTCCAACATCATCCGTGGATGGATCTTCGGTAC
CACTCTGGACAGCAAGACTCAGTCTCTGCTGATCGTGAACAACGCCACCA
ACGTGGTCATCAAGGTCTGCGAGTTCCAGTTCTGCAACGACCCCTTCCTGG
GAGTGTACTACCACAAGAACAACAAGTCATGGATGGAGTCCGAGTTCCGC
GTGTACTCTTCAGCTAACAACTGCACTTTCGAGTACGTCAGCCAGCCATTC
CTGATGGACCTGGAAGGAAAGCAGGGTAACTTCAAGAACCTGAGGGAGTT
CGTGTTCAAGAACATCGACGGTTACTTCAAGATCTACAGCAAGCACACCCC
CATCAACCTGGTGAGAGACCTGCCACAGGGATTCTCTGCTCTGGAACCCCT
GGTCGACCTGCCAATCGGTATCAACATCACCCGCTTCCAGACTCTGCTGGC
TCTGCACCGTTCCTACCTGACTCCTGGCGACTCCAGCTCTGGATGGACTGC
TGGAGCTGCTGCTTACTACGTGGGATACCTGCAGCCAAGGACCTTCCTGCT
GAAGTACAACGAGAACGGTACCATCACTGACGCCGTGGACTGCGCTCTGG
ACCCACTGTCAGAAACCAAGTGCACTCTGAAGTCCTTCACCGTCGAGAAG
GGTATCTACCAGACTAGCAACTTCAGGGTCCAGCCTACCGAATCTATCGTG
AGATTCCCAAACATCACTAACCTGTGCCCTTTCGGCGAGGTGTTCAACGCC
ACCAGATTCGCTTCCGTCTACGCCTGGAACAGGAAGAGAATCAGCAACTG
CGTGGCTGACTACTCTGTCCTGTACAACAGCGCCTCTTTCTCAACCTTCAA
GTGCTACGGCGTGTCACCTACTAAGCTGAACGACCTGTGCTTCACCAACGT
GTACGCCGACTCCTTCGTCATCAGGGGAGACGAGGTGAGACAGATCGCTC
CTGGCCAGACTGGAAAGATCGCCGACTACAACTACAAGCTGCCCGACGAC

FIG.16

TTCACCGGTTGCGTGATCGCTTGGAACAGCAACAACCTGGACTCTAAGGTC
GGTGGCAACTACAACTACCTGTACCGCCTGTTCCGTAAGAGCAACCTGAAG
CCCTTCGAGAGGGACATCAGCACTGAAATCTACCAGGCCGGATCTACCCCA
TGCAACGGTGTGGAAGGCTTCAACTGCTACTTCCCTCTGCAGTCTTACGGT
TTCCAGCCCACTAACGGTGTCGGCTACCAGCCATACAGAGTGGTCGTGCTG
AGCTTCGAGCTGCTGCACGCCCCTGCTACTGTGTGCGGTCCCAAGAAGTCT
ACCAACCTGGTGAAGAACAAGTGCGTCAACTTCAACTTCAACGGCCTGAC
CGGAACTGGTGTGCTGACCGAATCAAACAAGAAGTTCCTGCCTTTCCAGC
AGTTCGGCCGCGACATCGCTGACACCACTGACGCCGTCCGTGACCCACAG
ACCCTGGAGATCCTGGACATCACTCCTTGCTCATTCGGAGGTGTGTCCGTC
ATCACTCCCGGAACCAACACTTCCAACCAGGTGGCTGTCCTGTACCAGGAC
GTGAACTGCACTGAGGTGCCTGTGGCTATCCACGCTGACCAGCTGACCCCA
ACTTGGCGCGTCTACTCAACCGGCTCCAACGTGTTCCAGACTCGTGCTGGT
TGCCTGATCGGCGCCGAGCACGTCAACAACAGCTACGAATGCGACATCCCT
ATCGGCGCTGGAATCTGCGCCTCTTACCAGACCCAGACTAACAGCCCCCGC
AGGGCTAGGTCTGTGGCTTCCCAGAGCATCATCGCTTACACCATGTCACTG
GGTGCTGAAAACTCCGTCGCCTACAGCAACAACTCTATCGCCATCCCAACC
AACTTCACTATCTCAGTCACCACTGAGATCCTGCCTGTGAGCATGACCAAG
ACTTCTGTCGACTGCACTATGTACATCTGCGGCGACAGCACCGAATGCTCT
AACCTGCTGCTGCAGTACGGTTCCTTCTGCACCCAGCTGAACCGTGCTCTG
ACTGGCATCGCCGTGGAGCAGGACAAGAACACTCAGGAAGTGTTCGCTCA
GGTCAAGCAGATCTACAAGACCCCACCTATCAAGGACTTCGGCGGATTCAA
CTTCTCCCAGATCCTGCCAGACCCTTCAAAGCCCTCCAAGCGCAGCTTCAT
CGAAGACCTGCTGTTCAACAAGGTGACCCTGGCCGACGCTGGATTCATCA
AGCAGTACGGAGACTGCCTGGGTGACATCGCCGCTCGTGACCTGATCTGCG
CTCAGAAGTTCAACGGTCTGACCGTCCTGCCCCCACTGCTGACTGACGAG
ATGATCGCCCAGTACACTTCAGCCCTGCTGGCTGGTACCATCACTTCTGGAT
GGACCTTCGGTGCTGGTGCTGCTCTGCAGATCCCATTCGCTATGCAGATGG
CCTACCGTTTCAACGGAATCGGTGTGACCCAGAACGTCCTGTACGAAAACC
AGAAGCTGATCGCTAACCAGTTCAACAGCGCCATCGGCAAGATCCAGGAC
AGCCTGTCATCCACTGCCTCTGCTCTGGGAAAGCTGCAGGACGTCGTGAA
CCAGAACGCCCAGGCTCTGAACACCCTGGTGAAGCAGCTGAGCTCTAACT
TCGGAGCTATCTCATCCGTCCTGAACGACATCCTGTCTCGCCTGGACAAGG
TGGAGGCCGAAGTCCAGATCGACCGCCTGATCACTGGTCGTCTGCAGTCA

FIG. 16 continued

CTGCAGACCTACGTGACTCAGCAGCTGATCAGGGCCGCTGAAATCAGAGC
CTCCGCTAACCTGGCCGCTACCAAGATGTCAGAGTGCGTGCTGGGACAGTC
CAAGCGTGTCGACTTCTGCGGCAAGGGATACCACCTGATGTCATTCCCACA
GTCCGCTCCTCACGGCGTCGTGTTCCTGCACGTGACCTACGTCCCTGCCCA
GGAGAAGAACTTCACCACTGCCCCCGCTATCTGCCACGACGGCAAGGCTC
ACTTCCCTAGGGAAGGAGTGTTCGTCTCAAACGGTACCCACTGGTTCGTGA
CTCAGAGAAACTTCTACGAGCCCCAGATCATCACCACTGACAACACTTTCG
TCTCCGGCAACTGCGACGTCGTGATCGGAATCGTGAACAACACCGTCTACG
ACCCCCTGCAGCCAGAACTGGACTCATTCAAGGAGGAACTGGACAAGTAC
TTCAAGAACCACACCTCCCCAGACGTGGACCTGGGCGACATCTCAGGAAT
CAACGCTTCCGTCGTGAACATCCAGAAGGAGATCGACCGCCTGAACGAAG
TCGCCAAGAACCTGAACGAGAGCCTGATCGACCTGCAGGAGCTGGGCAAG
TACGAACAGTACATCAAGTGGCCTGGTGGCTCTGGAGGTTCAGGCGGATCC
GGTGGCAGCGGAGGTTCAACCTGCCCTCCCTGCCCTGCTCCAGAGCTGCT
GGGCGGACCTTCTGTGTTCCTGTTCCCACCTAAGCCCAAGGACACCCTGAT
GATCAGCCGTACCCCAGAAGTGACTTGCGTCGTGGTCGACGTCTCTCACGA
GGACCCTGAAGTCAAGTTCAACTGGTACGTGGACGGCGTGGAGGTCCACA
ACGCTAAGACCAAGCCTCGCGAGGAACAGTACAACTCAACTTACCGTGTG
GTCTCCGTGCTGACCGTCCTGCACCAGGACTGGCTGAACGGCAAGGAGTA
CAAGTGCAAGGTGTCAAACAAGGCCCTGCCTGCTCCCATCGAAAAGACTA
TCTCCAAGGCCAAGGGACAGCCTAGGGAGCCCCAGGTCTACACCCTGCCC
CCATCAAGAGAGGAAATGACCAAGAACCAGGTCTCCCTGACTTGCCTGGT
GAAGGGTTTCTACCCCTCAGACATCGCTGTGGAGTGGGAATCCAACGGCC
AGCCAGAAAACAACTACAAGACCACTCCTCCCGTGCTGGACTCAGACGGC
TCCTTCTTCCTGTACAGCAAGCTGACTGTCGACAAGTCTCGCTGGCAGCAG
GGAAACGTGTTCTCTTGCTCAGTCATGCACGAGGCTCTGCACAACCACTAC
ACCCAGAAGTCCCTGAGCCTGTCTCCCGGCAAGTAA

FIG.16 continued

IMMUNOGENIC COMPOSITION AND USE THEREOF

CROSS-REFERENCE TO RELATED APPLICATION

This non-provisional application claims priority under 35 U.S.C. § 119(e) on U.S. provisional Patent Application No. 63/019,442 filed on May 4, 2020, the entire contents of which are hereby incorporated by reference.

REFERENCE TO A SEQUENCE LIST

This application refers to a "Sequence list" listed below, which is provided as an electronic document, created on Jul. 30, 2021, entitled "Sequence_Listing.txt" and being 55,538 bytes in size, the "Sequence list" is incorporated herein by reference in its entirety.

BACKGROUND OF THE INVENTION

1. Field of the Invention

The present disclosure relates to an immunogenic composition and a use thereof and in particular to an immunogenic composition and a use thereof against Coronavirus.

2. Description of the Related Art

Coronavirus Disease 2019 (COVID-19) is an infectious disease caused by Severe Acute Respiratory Syndrome Coronavirus 2 (hereinafter referred to as SARS-CoV-2). The emergence of SARS-CoV-2 has raised serious concerns due to the virus has rapidly distributed worldwide and resulted in the World Health Organization (WHO) declaring a global health emergency on 30 Jan. 2020. Therefore, there is an urgent need to develop an effective vaccine for the preparedness against the COVID-19.

SARS-CoV-2 are positive-sense single-stranded RNA viruses belonging to the betacoronavirus (beta-CoVs) of the subfamily Orthocoronavirinae, in the family Coronaviridae of the order Nidovirales ((2018). Arch. Virol. 163, 2601-2631). Severe acute respiratory syndrome coronavirus (SARS-CoV) and Middle East respiratory syndrome coronavirus (MERS-CoV) also belong to the beta-CoVs (N Engl J Med. 2003 May 15; 348(20):1967-76; N Engl J Med. 2012 Nov. 8; 367(19):1814-20.). Especially, both SARS-CoV and SARS-CoV-2 viruses entry into the host cells mediated by interaction of the receptor-binding domain (RBD) in S protein located on virus outer-membrane and angiotensin-converting enzyme 2 (ACE2) on cell.

BRIEF SUMMARY OF THE INVENTION

An object of the present invention is to provide an immunogenic composition, the immunogenic composition comprises a recombinant protein including a sequence selected from the group consisting of SEQ ID NO: 1, SEQ ID NO: 2, SEQ ID NO: 3, SEQ ID NO: 4, and any polypeptide encoded by a polynucleotide which is at least 80% homologous with SEQ ID NO: 1-4, wherein the recombinant protein contains an IgG1 Fc protein fragment having a length of at least 6 amino acids; or a nucleic acid molecule encoding the recombinant protein.

The immunogenic composition described above, wherein the IgG1 Fc protein fragment has a length of between 12-18 amino acids.

The immunogenic composition described above, wherein the recombinant protein fuses with a secreted signal peptide.

The immunogenic composition described above further comprises immunogenic compounds, adjuvants, pharmaceutically acceptable carriers, stabilisers or preservatives.

To achieve the above and other objects, the present invention provides a SARS-CoV-2 vaccine. The SARS-CoV-2 vaccine comprises a recombinant protein including a sequence selected from the group consisting of SEQ ID NO: 1, SEQ ID NO: 2, SEQ ID NO: 3, SEQ ID NO: 4, and any polypeptide encoded by a polynucleotide which is at least 80% homologous with SEQ ID NO: 1-4, wherein the recombinant protein contains an IgG1 Fc protein fragment having a length of at least 6 amino acids; or a nucleic acid molecule encoding the recombinant protein.

The vaccine described above, wherein the IgG1 Fc protein fragment has a length of between 12-18 amino acids.

The vaccine described above, wherein the recombinant protein fuses with nucleocapsid phosphoprotein protein of SARS-CoV-2, envelope protein of SARS-CoV-2 or membrane protein of SARS-CoV-2.

The vaccine described above, wherein the recombinant protein encoded by the nucleic acid molecule fuses with nucleocapsid phosphoprotein protein of SARS-CoV-2, envelope protein of SARS-CoV-2 or membrane protein of SARS-CoV-2.

The vaccine described above further comprises immunogenic compounds, adjuvants, pharmaceutically acceptable carriers, stabilisers or preservatives.

To achieve the above and other objects, the present invention provides a vector. The vector comprises a nucleic acid molecule encoding a recombinant protein including a sequence selected from the group consisting of SEQ ID NO: 1, SEQ ID NO: 2, SEQ ID NO: 3, SEQ ID NO: 4, and any polypeptide encoded by the polynucleotide which is at least 80% homologous with SEQ ID NO: 1-4, wherein the recombinant protein contains an IgG1 Fc protein fragment having a length of at least 6 amino acids.

The vector described above, wherein the recombinant protein encoded by the nucleic acid molecule fuses with nucleocapsid phosphoprotein protein of SARS-CoV-2, envelope protein of SARS-CoV-2 or membrane protein of SARS-CoV-2.

The vector described above, wherein the vector is selected from the group consisting of baculovirus, vaccinia virus, avipoxvirus, adenovirus, alphavirus, rhabdovirus, and herpesvirus.

The vector described above, wherein the vector is baculovirus.

To achieve the above and other objects, the present invention provides a method of inducing an immune response against SARS-CoV-2, the method comprises administering to a subject in need thereof the above immunogenic composition.

To achieve the above and other objects, the present invention provides a method of inducing an immune response against SARS-CoV-2, the method comprises administering to a subject in need thereof the above vaccine.

To achieve the above and other objects, the present invention provides a method of inducing an immune response against SARS-CoV-2, the method comprises administering to a subject in need thereof the above vector.

To achieve the above and other objects, the present invention provides a immunogenic composition comprising a nucleic acid molecule including a sequence selected from the group consisting of SEQ ID NO: 6, SEQ ID NO: 7, SEQ ID NO: 8 and SEQ ID NO: 9.

The above immunogenic composition, vaccine and vector can induce neutralizing antibodies against SARS-CoV-2 virus and be used against the coronavirus disease 2019 (COVID-19).

BRIEF DESCRIPTION OF THE DRAWINGS

FIG. 1 shows the amino acid sequence of RBD-Fc (SEQ ID NO: 1).

FIG. 2 shows the amino acid sequence of S2ΔTM-Fc (SEQ ID NO: 2).

FIG. 3 shows the amino acid sequence of S1-Fc (SEQ ID NO: 3).

FIG. 4 shows the amino acid sequence of SΔTM-Fc (SEQ ID NO: 4).

FIG. 12 shows the amino acid sequence of nucleocapsid phosphoprotein protein (SEQ ID NO: 10), envelope protein (SEQ ID NO: 11) and membrane protein (SEQ ID NO: 12) of SARS-CoV-2.

FIG. 13 shows the DNA sequence of RBD-Fc (SEQ ID NO: 6).

FIG. 14 shows the DNA sequence of S2 ΔTM-Fc (SEQ ID NO: 7).

FIG. 15 shows the DNA sequence of S1-Fc (SEQ ID NO: 8).

FIG. 16 shows the DNA sequence of SΔTM-Fc (SEQ ID NO: 9).

DETAILED DESCRIPTION OF THE INVENTION

To facilitate understanding of the object, characteristics and effects of this present disclosure, embodiments together with the attached drawings for the detailed description of the present disclosure are provided.

Expression of Vaccine Candidates

First, DNA sequences of four vaccine candidates which encode recombinant protein RBD-Fc, S2 ΔTM-Fc, S1-Fc and SΔTM-Fc are designed. FIG. 13 shows the DNA sequence of RBD-Fc. FIG. 14 shows the DNA sequence of S2Δ TM-Fc. FIG. 15 shows the DNA sequence of S1-Fc. FIG. 16 shows the DNA sequence of SΔTM-Fc.

Figures 5, 6:
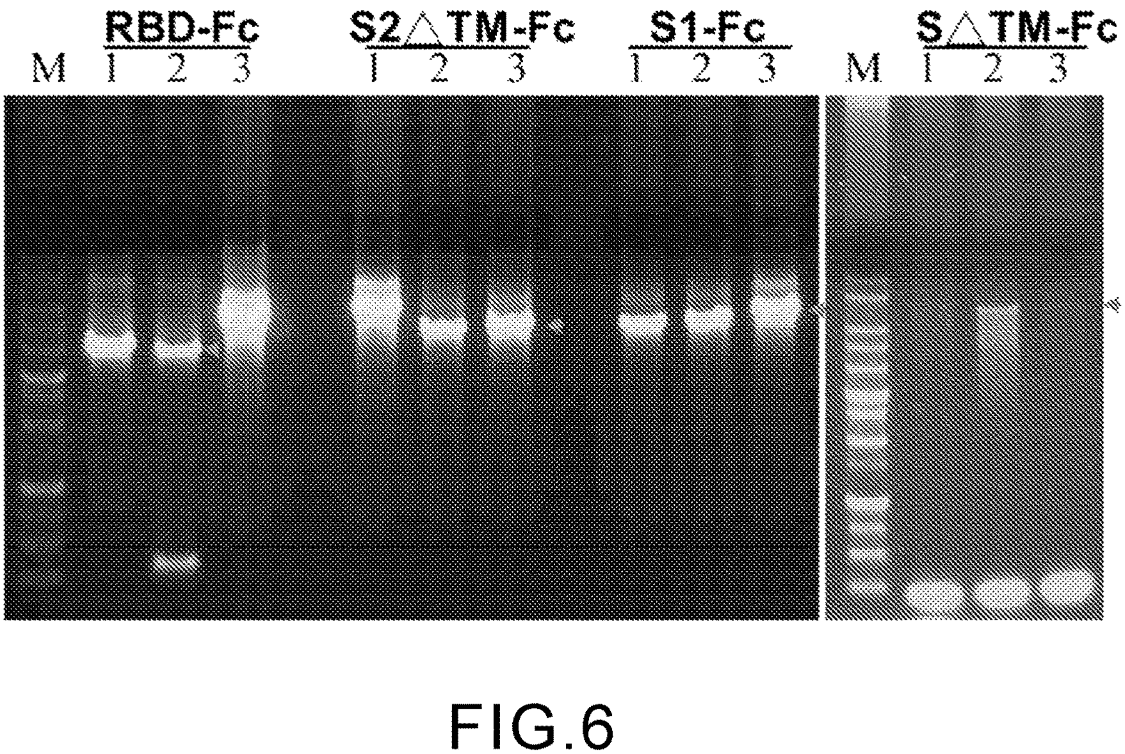
FIG. 5 shows the amino acid sequence of secreted signal peptide (SEQ ID NO: 5).
FIG. 6 shows the DNA gel electrophoresis image of RBD-Fc, S2 ΔTM-Fc, S1-Fc and SΔTM-Fc.

The vaccine candidates are designed according to the amino acid sequences of SARS-CoV-2 spike protein (Accession number: NC_045512). Herein, RBD-Fc represents the receptor binding domain of spike protein of SARS-CoV-2 fused with human IgG1 constant heavy chain 2 and constant heavy chain 3 (Fc protein), the amino acid sequence of RBD-Fc is shown in FIG. 1; S2 ΔTM-Fc represents the S2 subunit of spike protein of SARS-CoV-2 deleting the transmembrane protein and fused with Fc protein, the amino acid sequence of S2Δ TM-Fc is shown in FIG. 2; S1-Fc represents the S1 subunit of spike protein of SARS-CoV-2 fused with Fc protein, the amino acid sequence of S1-Fc is shown in FIG. 3; SΔTM-Fc represents the spike protein of SARS-CoV-2 deleting the transmembrane protein and fused with Fc protein, the amino acid sequence of SΔ TM-Fc is shown in FIG. 4. For the purpose of vaccine production, all the constructs of the vaccine candidates are fused with a secreted signal peptide, the secreted signal peptide is located at the N-terminal end of the recombinant protein and the Fc sequence is located at the C-terminal end of the recombinant protein. The amino acid sequence of secreted signal peptide is shown in FIG. 5. However, in other embodiments, the secreted signal peptide is not necessary.

Next, the above DNA sequences of four vaccine candidates are cloned into pFastBac 1 vector separately. In other embodiments, the vector may be selected from vaccinia virus, avipoxvirus, adenovirus, alphavirus, rhabdovirus, herpesvirus or other known suitable vector system.

Four pFastBac 1 vectors containing each of the above DNA sequences of vaccine candidates separately are transformed into the *E. coli* strain DH10Bac for production of the recombinant Bacmid DNA which contains the above DNA sequences of four vaccine candidates. The recombinant Bacmid DNA is identified by PCR analysis. As shown in FIG. 6, "M" indicates the molecular weight marker, the numerals "1", "2" and "3" indicate the serial number of *E. coli* colonies therefrom the above recombinant Bacmid DNA is obtained, the theoretic recombinant Bacmid DNA sizes of RBD-Fc, S2 ΔTM-Fc, S1-Fc and SΔTM-Fc are 3,809 bps, 4,700 bps, 5,159 bps and 6,743 bps respectively. The determined recombinant Bacmid DNA sizes of RBD-Fc, S2 ΔTM-Fc, S1-Fc and SΔTM-Fc are 3,900 bps, 4,800 bps, 5,200 bps and 6,800 bps respectively, corresponding to the above theoretic recombinant Bacmid DNA sizes. The above transformation and PCR analysis of the recombinant Bacmid DNA are performed according to Bac-to-Bac™ Baculovirus Expression System USER GUIDE.

Then, the recombinant Bacmid DNA which contains each of the above DNA sequences of four vaccine candidates are separately transfected into *S. frugiperda* cells (sf9 cell) for baculovirus production. The baculovirus is identified by DNA sequencing. The above transfection of the recombinant Bacmid DNA is performed according to Bac-to-Bac™ Baculovirus Expression System USER GUIDE.

Figure 7:
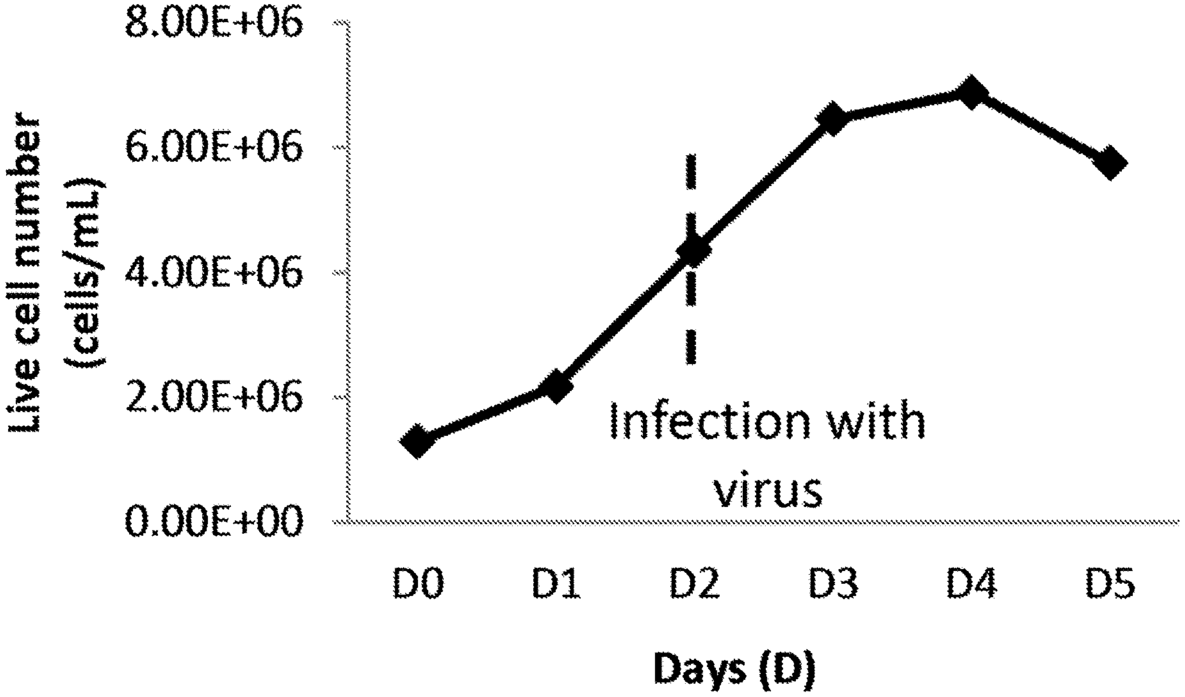
FIG. 7 shows the trend of cell expansion infected with viruses.
Figure 8:
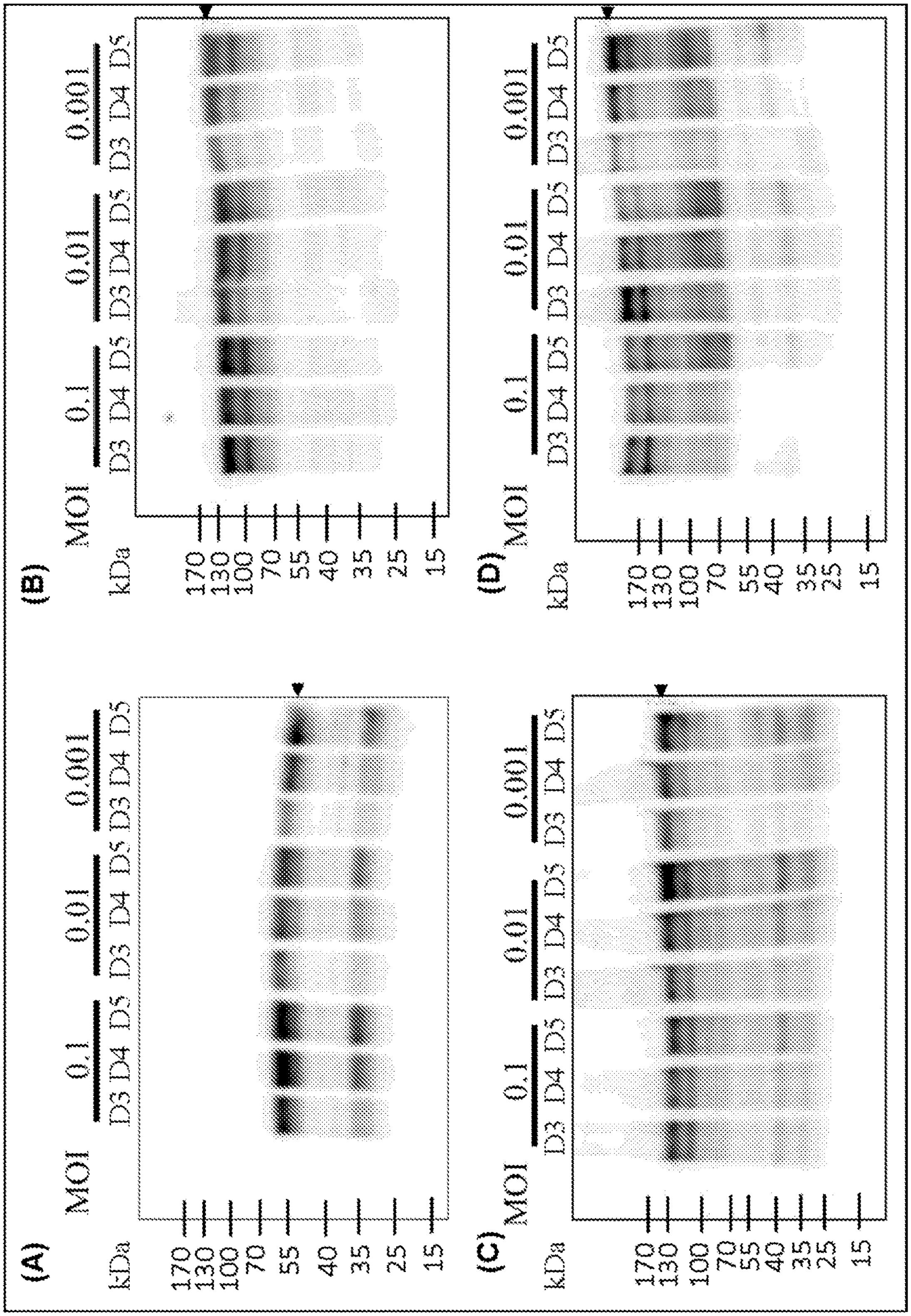
FIG. 8 shows the expression levels of vaccine candidates in western blot image at 3rd day, 4th day and 5th day after infection. (A) RBD-Fc (B) S2 ΔTM-Fc (C) S1-Fc (D) SΔTM-Fc.

Finally, Sf9 cells are infected with baculovirus containing the above DNA sequences of four vaccine candidates with multiplicity of infection (MOI) of 0.1, 0.001 and 0.0001 separately for five days, the trend of cell expansion infected with viruses are shown in FIG. 7. At the time point of 3rd day, 4th day and 5th day post infection, the infected Sf9 cells are collected for checking the expression levels of vaccine candidates, proteins synthesized in the infected Sf9 cells are detected by western blot, the result is shown in FIG. 8, the location of protein standards and their size in kilodaltons (kda) indicated that the 55 kda (A: RBD-Fc), 110 kda (B: S2 ΔTM-Fc), 130 kda (C: S1-Fc) and 170 kda (D: SΔTM-Fc) recombinant protein portion are the major proteins being synthesized in the cells. The above western blotting is performed according to the reference "A Guide to Polyacrylamide Gel Electrophoresis and detection (Bio-Rad)".

Production of Vaccine Candidates

Sf9 cells are prepared, sf9 cells are grown at 27° C. to a density of 3.5~5×$10^6$ cells/mL in insect-XPRESS Protein-free media (Lonza Ltd). sf9 cells are infected by the baculovirus expression vectors containing the above DNA sequences of four vaccine candidates at a multiplicity of infection (MOI) of 0.1~0.001 for production of four vaccine candidates. During infection of sf9 cells, the vaccine candidates are produced under the transcriptional control of the baculovirus polyhedrin promoter. Sf9 cells are harvested 72~96 hours post-infection by centrifugation for 15 minutes at 6,000×g. The supernatant of Sf9 cells is stored at 4° C.

Purification of Vaccine Candidate RBD-Fc

In this embodiment, the purification of RBD-Fc which is non-denatured and suitable as a component of a coronavirus vaccine for human use being performed by protein A affinity chromatography. The following procedure is used to purify the RBD-Fc from sf9 cells infected with the recombinant baculovirus.

2 L culture broth of the infected sf9 cells containing RBD-Fc is prepared according to the above procedure of "expression of vaccine candidates", the initial cell concentration of the sf9 cells to be infected is 1.0×$10^6$ cells/mL, the sf9 cells are then infected for three days until the infected cell concentration of the sf9 cells achieve 4.0×$10^6$ cells/mL (viability 40-60%, MOI=0.1). The culture broth of the infected sf9 cells is centrifuged with 9000×g for 20 minutes to obtain the supernatant, and the supernatant is filtered with a filter (0.22 μm pore size) to obtain a sample liquid.

A pharmacia XK 16/40 column filled with 20 mL Protein A resin (Eshmuno A, Merck Millipore) is prepared and mounted on AKTA Pure chromatography system. The above sample liquid is applied to the columns at a flow rate of 20 mL/minute (PreC: 0.30 Mpa), the flow through liquid is collected. After loading the above sample liquid into the column, the column is further washed with PBS (pH 7.3), until the UV absorption at 280 nm of the wash liquid returns to baseline. The wash liquid through the column is collected. After washing the column, Citric acid solution (0.3 M) as the elute is loaded into the column to obtain the elute containing RBD-Fc which binds to Protein A.

Since the contaminated protein also flows through the column into the elute, the previous elute containing RBD-Fc is eluted again from the Protein A resin column with approximately 5 fold column volume of 100 mM citrate acid (pH 3.0), and the eluent is neutralized with 1M Tris-HCl (pH 9.0). The sample liquid, the flow through liquid, the wash liquid and the elute are analyzed by SDS-PAGE as follows. The proteins in the sample liquid, the flow through liquid, the wash liquid and the elute are disrupted in a boiling water bath for 10 minutes in the presence of 2% sodium dodecyl sulfate and 5% beta-mercaptoethanol, and then analyzed by SDS-PAGE (10% polyacrylamide gel in the presence of 0.1% SDS), finally stained with Coomassie blue. The SDS-PAGE analysis is performed according to the reference "A Guide to Polyacrylamide Gel Electrophoresis and detection (Bio-Rad)".

The purification of S2 ΔTM-Fc, S1-Fc and SΔTM-Fc is performed by the same procedure as the purification of RBD-Fc.

Figure 9:
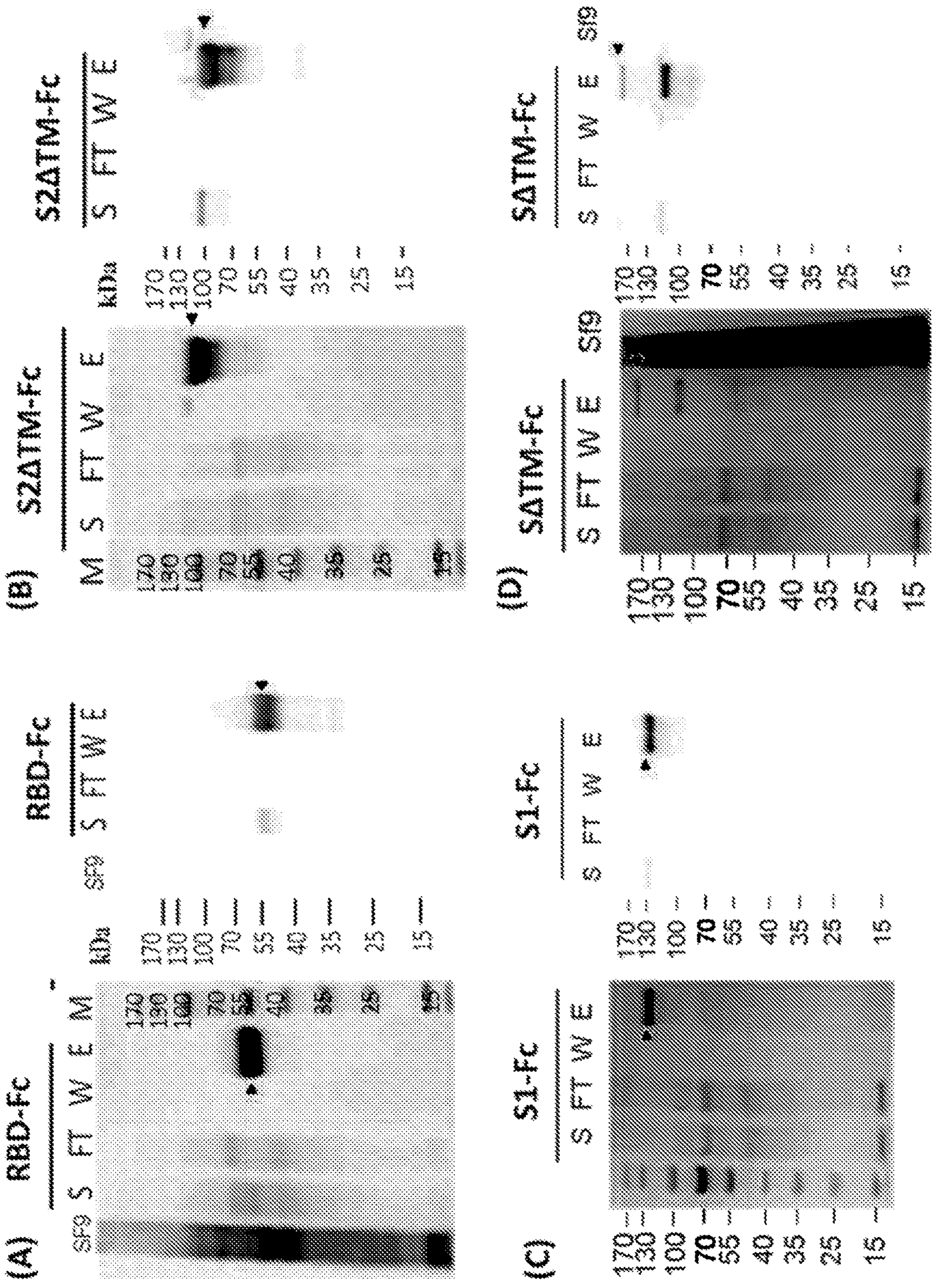
FIG. 9 shows the SDS-PEGE (left) and western blot (right) image of purified vaccine candidates. Arrows indicates the expected position of expressed protein. (A) RBD-Fc (B) S2 ΔTM-Fc (C) S1-Fc (D) SΔTM-Fc (S) sample liquid (FT) flow through liquid (W) wash liquid (E) elute.

The result of purification of four vaccine candidates is shown in FIG. 9. The purified vaccine candidates are obtained by the above procedure.

In other embodiment, other known technologies of protein purification are utilized to purify the above vaccine candidates.

Plaque Reduction Neutralization Test (PRNT) of the Antisera from Immunized Mice Against SARS-CoV-2 Virus First, twelve groups of C57BL/6 mice (7 weeks old, female, weight is 18~22 gram) are prepared, each group contains ten mice, five groups of mice are immunized three times by intramuscular injection of 20 μg of vaccine candidates in 50 μl of PBS; five groups of mice are immunized three times by intramuscular injection of 20 μg of vaccine candidates in 50 μl of PBS containing aluminum hydroxide as an adjuvant; one group of mice are injected 50 μl of PBS containing aluminum hydroxide three times by intramuscular injection; one group of mice are merely injected 50 μl of PBS three times by intramuscular injection. The immunized condition is listed in the table 1.

TABLE 1

| Group numbers | Antigens | μg/dose | Adjuvant |
|---|---|---|---|
| 1 | RBD-Fc | 20 | — |
| 2 | S2ΔTM-Fc | | — |
| 3 | S1-Fc | | — |
| 4 | RBD-Fc + S2ΔTM-Fc | | — |
| 5 | S2ΔTM-Fc + S1-Fc | | — |
| 6 | — | | — |
| 7 | RBD-Fc | | $Al(OH)_3$* |
| 8 | S2ΔTM-Fc | | $Al(OH)_3$* |
| 9 | S1-Fc | | $Al(OH)_3$* |
| 10 | RBD-Fc + S2ΔTM-Fc | | $Al(OH)_3$* |
| 11 | S2ΔTM-Fc + S1-Fc | | $Al(OH)_3$* |
| 12 | — | | $Al(OH)_3$* |

*The quantity of adjuvant is 500 μg/dose

Figure 10:
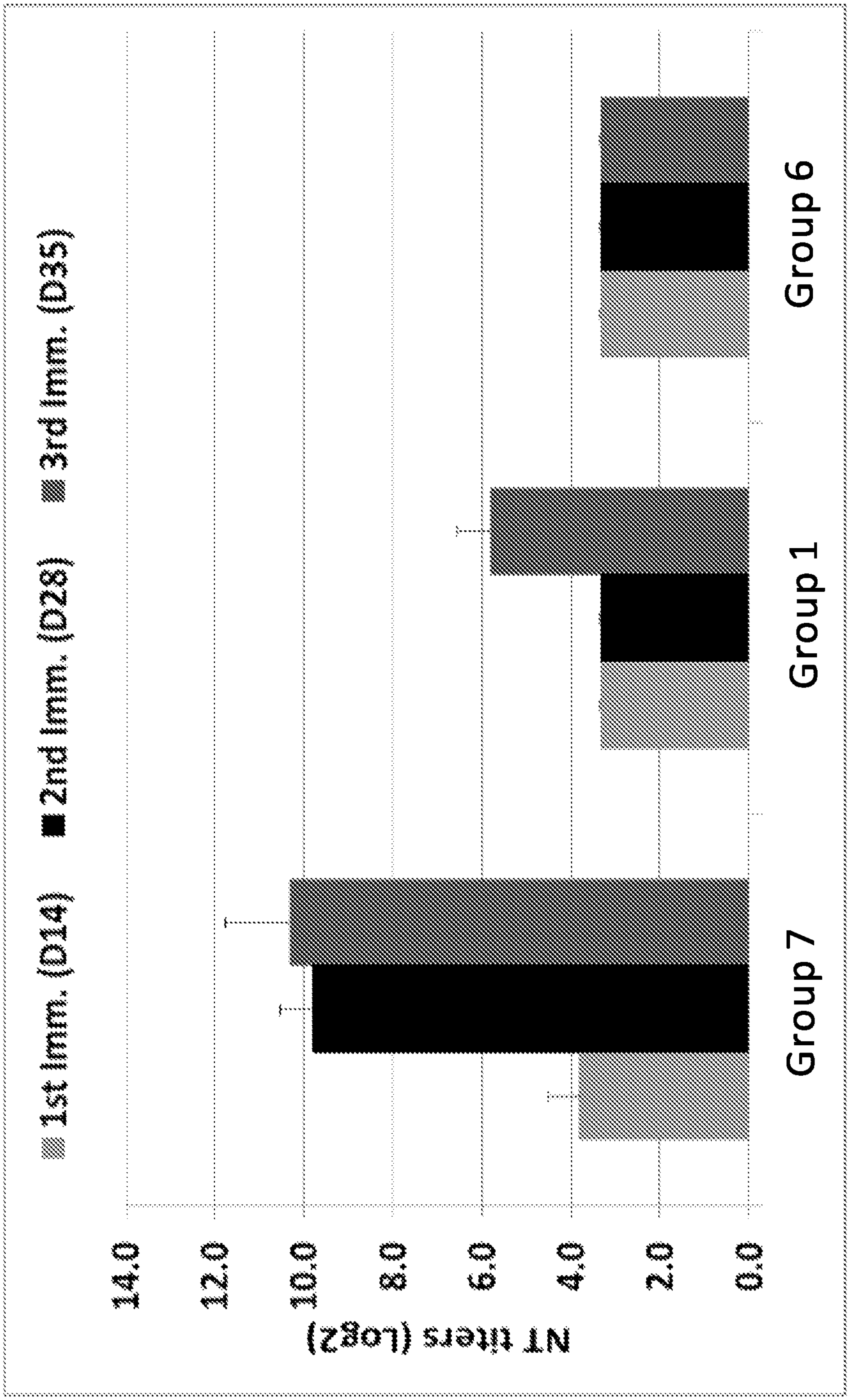
FIG. 10 shows the neutralizing antibody titers in sera which are blood sampled from the immunized mice.

Next, at the time point of immunization, mice of groups 1, 6 and 7 are blood sampled to detect neutralizing antibody titers. The result is shown in FIG. 10, mice of group 7 which are administered by RBD-Fc and an adjuvant has the higher titer.

Figure 11:
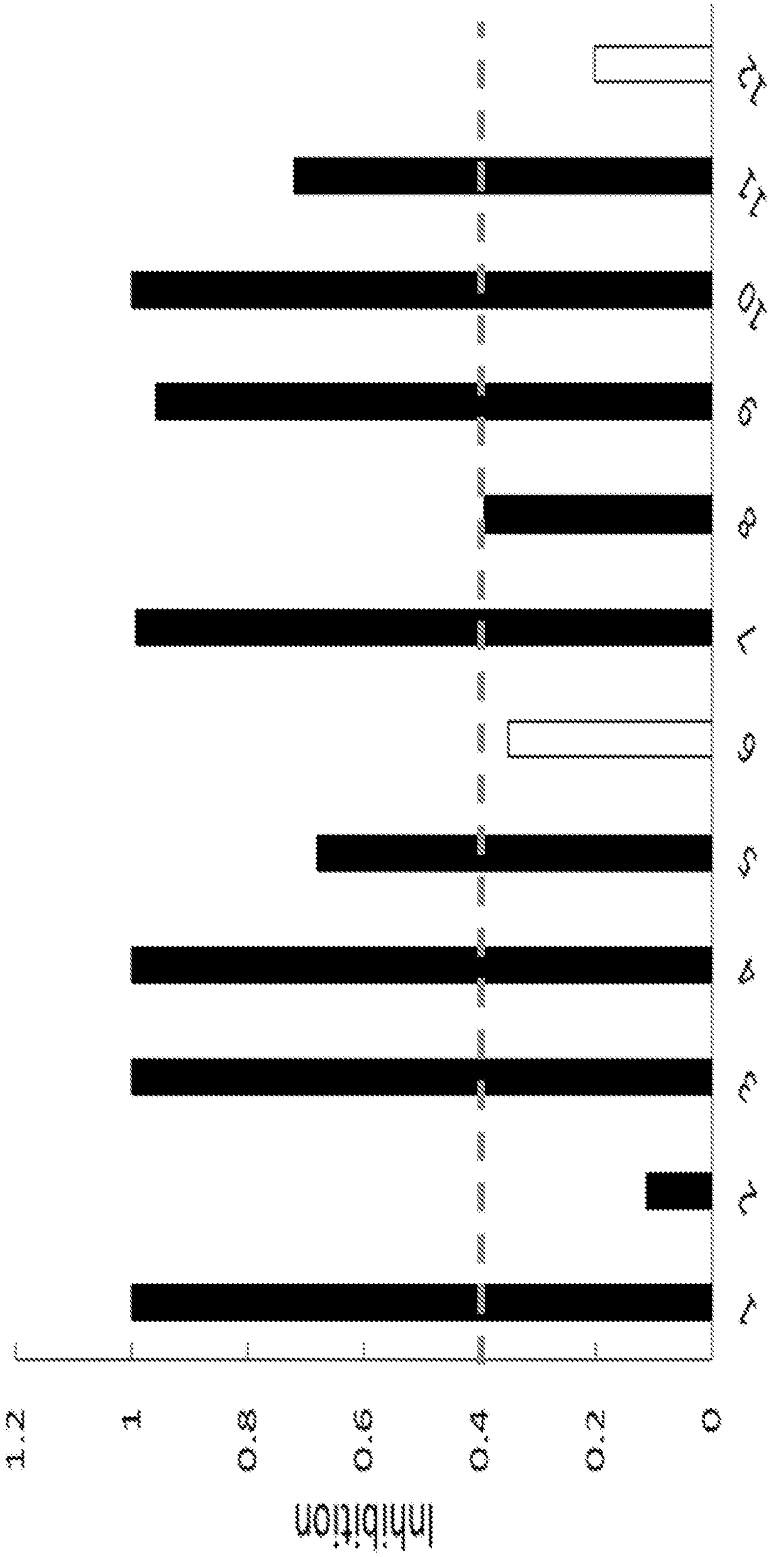
FIG. 11 shows the result of plaque reduction neutralization test (PRNT) of the antisera from immunized mice against SARS-CoV-2 virus.

Finally, twelve groups of vero E6 cells monolayer are pre-seeded in twelve wells of a 24-well plate as the experimental groups. 0.1 mL of twelve test sera (5120-fold dilution) obtained from the above mice that are immunized three times are separately mixed with 100 PFU/0.1 mL of SARS-CoV-2 virus (provided by Professor Sui-Yuan Chang, Department of Clinical Laboratory Sciences and Medical Biotechnology, College of Medicine, National Taiwan University) and co-incubated at 37° C. for 60 minutes. Then, twelve mixtures of SARS-CoV-2 and test sera are separately added into twelve experimental groups. Meanwhile, two positive control wells (vero E6 cells are co-incubated with 100 PFU of SARS-CoV-2 virus without the above sera at 37° C. for 60 minutes) are established for each assay as the positive control group to ensure infectivity of the cell monolayer. Subsequently, the medium of twelve experimental groups and two positive control groups are removed, twelve experimental groups and two positive control groups are then added with overlay medium. The 24-well plate with the experimental groups and positive control groups is incubated at 37° C. in 5% $CO_2$ for six days and plaques were counted on the 6th day. The result of plaque reduction neutralization test is shown in FIG. 11; it demonstrates that when the experimental group contains the RBD domain fused with Fc protein (groups 1, 3-5, 7 and 9-10) it can effectively induce neutralizing antibodies against SARS-CoV-2 virus, the efficacy of the experimental groups containing the RBD domain fused with Fc protein and adjuvant are better, and the combination of S2 ΔTM-Fc fused with Fc protein and adjuvant can also induce neutralizing antibodies against SARS-CoV-2 virus.

Furthermore, a SARS-CoV-2 recombinant protein fragment used for SARS-CoV-2 is able to be designed at least 80%, 81%, 82%, 83%, 84%, 85%, 86%, 87%, 88%, 89%, 90%, 91%, 92%, 93%, 94%, 95%, 96%, 97%, 98%, or 99%) identical to the RBD, S1 protein, S2 protein or spike protein; a Fc protein fragment used for SARS-CoV-2 is able to be designed to has a length of at least 6 amino acids, and preferably has a length of between 12 and 18 amino acids. The length of Fc protein fragment may be 6, 7, 8, 9, 10, 11, 12, 13, 14, 15, 16, 17 or 18 amino acids.

FIG. 12 shows the amino acid sequence of nucleocapsid phosphoprotein protein, envelope protein and membrane protein of SARS-CoV-2. For the use of COVID-19 vaccine, the nucleocapsid phosphoprotein protein, envelope protein or membrane protein of SARS-CoV-2 are also able to be designed as a part of COVID-19 vaccine, that is, nucleocapsid phosphoprotein protein, envelope protein and membrane protein of SARS-CoV-2 can be fused with the above vaccine candidates.

As used herein, "percent homology" of two amino acid sequences is determined using the algorithm described in Karlin and Altschul, Proc, Natl. Acad. Sci. USA 87:2264-2268, 1990, modified as described in Karlin and Altschul, Proc, Natl. Acad. Sci. USA 90:5873-5877, 1993. Such an algorithm is incorporated into the NBLAST and XBLAST programs of Altschul et al., J. Mol. Biol. 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., Nucleic Acids Res. 25:3389-3402, 1997. When utilizing the BLAST and Gapped BLAST programs, the default parameters of the respective programs (e.g., XBLAST and NBLAST) are used. See www.ncbi.nlm.nih.gov.

As mentioned above, SARS-CoV-2 recombinant proteins fused with Fc protein can induce neutralizing antibodies against SARS-CoV-2 virus and it can be used as a vaccine against the coronavirus disease 2019 (COVID-19).

While the present disclosure has been described by means of specific embodiments, numerous modifications and variations could be made thereto by those skilled in the art without departing from the scope and spirit of the present disclosure set forth in the claims.

What is claimed is:

1. A immunogenic composition comprising:

a recombinant protein including a sequence selected from the group consisting of SEQ ID NO: 1, SEQ ID NO: 2, SEQ ID NO: 3, and SEQ ID NO: 4; or a nucleic acid molecule encoding the recombinant protein.

2. The immunogenic composition of claim 1, wherein the recombinant protein is fused with a secreted signal peptide.

3. The immunogenic composition of claim 1, further comprising immunogenic compounds, adjuvants, pharmaceutically acceptable carriers, stabilisers or preservatives.

4. A SARS-CoV-2 vaccine comprising:

a recombinant protein including a sequence selected from the group consisting of SEQ ID NO: 1, SEQ ID NO: 2, SEQ ID NO: 3, and SEQ ID NO: 4; or a nucleic acid molecule encoding the recombinant protein.

5. The vaccine of claim 4, wherein the recombinant protein is fused with nucleocapsid phosphoprotein protein of SARS-CoV-2, envelope protein of SARS-CoV-2 or membrane protein of SARS-CoV-2.

6. The vaccine of claim 4, wherein the recombinant protein encoded by the nucleic acid molecule is fused with nucleocapsid phosphoprotein protein of SARS-CoV-2, envelope protein of SARS-CoV-2 or membrane protein of SARS-CoV-2.

7. The vaccine of claim 4, further comprising immunogenic compounds, adjuvants, pharmaceutically acceptable carriers, stabilisers or preservatives.

8. A vector comprising a nucleic acid molecule encoding a recombinant protein including a sequence selected from the group consisting of SEQ ID NO: 1, SEQ ID NO: 2, SEQ ID NO: 3, and SEQ ID NO: 4.

9. The vector of claim 8, wherein the recombinant protein encoded by the nucleic acid molecule is fused with nucleocapsid phosphoprotein protein of SARS-CoV-2, envelope protein of SARS-CoV-2 or membrane protein of SARS-CoV-2.

10. The vector of claim 8, wherein the vector is selected from the group consisting of baculovirus, vaccinia virus, avipoxvirus, adenovirus, alphavirus, rhabdovirus, and herpesvirus.

11. The vector of claim 10, wherein the vector is baculovirus.

12. A method of inducing an immune response against SARS-CoV-2, comprising administering to a subject in need thereof the immunogenic composition of claim 1.

13. A method of inducing an immune response against SARS-CoV-2, comprising administering to a subject in need thereof the vaccine of claim 4.

14. A method of inducing an immune response against SARS-CoV-2, comprising administering to a subject in need thereof the vector of claim 8.

15. A immunogenic composition comprising:

a nucleic acid molecule including a sequence selected from the group consisting of SEQ ID NO: 6, SEQ ID NO: 7, SEQ ID NO: 8 and SEQ ID NO: 9.

* * * * *

SEQUENCE LISTING

```
<160> NUMBER OF SEQ ID NOS: 12

<210> SEQ ID NO 1
<211> LENGTH: 458
<212> TYPE: PRT
<213> ORGANISM: Artificial Sequence
<220> FEATURE:
<223> OTHER INFORMATION: Recombinant Spike Protein

<400> SEQUENCE: 1

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn Leu Val Lys Asn Lys Cys
        195                 200                 205
```

-continued

```
Val Asn Phe Asn Phe Asn Gly Leu Thr Gly Thr Gly Gly Gly Ser Gly
    210                 215                 220

Gly Ser Gly Gly Ser Gly Gly Ser Gly Gly Ser Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 2
<211> LENGTH: 755
<212> TYPE: PRT
<213> ORGANISM: Artificial Sequence
<220> FEATURE:
<223> OTHER INFORMATION: Recombinant Spike Protein

<400> SEQUENCE: 2

Met Ser Leu Gly Ala Glu Asn Ser Val Ala Tyr Ser Asn Asn Ser Ile
1               5                   10                  15

Ala Ile Pro Thr Asn Phe Thr Ile Ser Val Thr Thr Glu Ile Leu Pro
            20                  25                  30

Val Ser Met Thr Lys Thr Ser Val Asp Cys Thr Met Tyr Ile Cys Gly
        35                  40                  45

Asp Ser Thr Glu Cys Ser Asn Leu Leu Leu Gln Tyr Gly Ser Phe Cys
    50                  55                  60

Thr Gln Leu Asn Arg Ala Leu Thr Gly Ile Ala Val Glu Gln Asp Lys
65                  70                  75                  80

Asn Thr Gln Glu Val Phe Ala Gln Val Lys Gln Ile Tyr Lys Thr Pro
                85                  90                  95

Pro Ile Lys Asp Phe Gly Gly Phe Asn Phe Ser Gln Ile Leu Pro Asp
            100                 105                 110
```

-continued

```
Pro Ser Lys Pro Ser Lys Arg Ser Phe Ile Glu Asp Leu Leu Phe Asn
        115                 120                 125

Lys Val Thr Leu Ala Asp Ala Gly Phe Ile Lys Gln Tyr Gly Asp Cys
    130                 135                 140

Leu Gly Asp Ile Ala Ala Arg Asp Leu Ile Cys Ala Gln Lys Phe Asn
145                 150                 155                 160

Gly Leu Thr Val Leu Pro Pro Leu Leu Thr Asp Glu Met Ile Ala Gln
                165                 170                 175

Tyr Thr Ser Ala Leu Leu Ala Gly Thr Ile Thr Ser Gly Trp Thr Phe
            180                 185                 190

Gly Ala Gly Ala Ala Leu Gln Ile Pro Phe Ala Met Gln Met Ala Tyr
        195                 200                 205

Arg Phe Asn Gly Ile Gly Val Thr Gln Asn Val Leu Tyr Glu Asn Gln
    210                 215                 220

Lys Leu Ile Ala Asn Gln Phe Asn Ser Ala Ile Gly Lys Ile Gln Asp
225                 230                 235                 240

Ser Leu Ser Ser Thr Ala Ser Ala Leu Gly Lys Leu Gln Asp Val Val
                245                 250                 255

Asn Gln Asn Ala Gln Ala Leu Asn Thr Leu Val Lys Gln Leu Ser Ser
            260                 265                 270

Asn Phe Gly Ala Ile Ser Ser Val Leu Asn Asp Ile Leu Ser Arg Leu
        275                 280                 285

Asp Lys Val Glu Ala Glu Val Gln Ile Asp Arg Leu Ile Thr Gly Arg
    290                 295                 300

Leu Gln Ser Leu Gln Thr Tyr Val Thr Gln Gln Leu Ile Arg Ala Ala
305                 310                 315                 320

Glu Ile Arg Ala Ser Ala Asn Leu Ala Ala Thr Lys Met Ser Glu Cys
                325                 330                 335

Val Leu Gly Gln Ser Lys Arg Val Asp Phe Cys Gly Lys Gly Tyr His
            340                 345                 350

Leu Met Ser Phe Pro Gln Ser Ala Pro His Gly Val Val Phe Leu His
        355                 360                 365

Val Thr Tyr Val Pro Ala Gln Glu Lys Asn Phe Thr Thr Ala Pro Ala
    370                 375                 380

Ile Cys His Asp Gly Lys Ala His Phe Pro Arg Glu Gly Val Phe Val
385                 390                 395                 400

Ser Asn Gly Thr His Trp Phe Val Thr Gln Arg Asn Phe Tyr Glu Pro
                405                 410                 415

Gln Ile Ile Thr Thr Asp Asn Thr Phe Val Ser Gly Asn Cys Asp Val
            420                 425                 430

Val Ile Gly Ile Val Asn Asn Thr Val Tyr Asp Pro Leu Gln Pro Glu
        435                 440                 445

Leu Asp Ser Phe Lys Glu Glu Leu Asp Lys Tyr Phe Lys Asn His Thr
    450                 455                 460

Ser Pro Asp Val Asp Leu Gly Asp Ile Ser Gly Ile Asn Ala Ser Val
465                 470                 475                 480

Val Asn Ile Gln Lys Glu Ile Asp Arg Leu Asn Glu Val Ala Lys Asn
                485                 490                 495

Leu Asn Glu Ser Leu Ile Asp Leu Gln Glu Leu Gly Lys Tyr Glu Gln
            500                 505                 510

Tyr Ile Lys Trp Pro Gly Gly Ser Gly Gly Ser Gly Gly Ser Gly Gly
        515                 520                 525

Ser Gly Gly Ser Thr Cys Pro Pro Cys Pro Ala Pro Glu Leu Leu Gly
```

```
    530                 535                 540

Gly Pro Ser Val Phe Leu Phe Pro Pro Lys Pro Lys Asp Thr Leu Met
545                 550                 555                 560

Ile Ser Arg Thr Pro Glu Val Thr Cys Val Val Val Asp Val Ser His
                565                 570                 575

Glu Asp Pro Glu Val Lys Phe Asn Trp Tyr Val Asp Gly Val Glu Val
            580                 585                 590

His Asn Ala Lys Thr Lys Pro Arg Glu Glu Gln Tyr Asn Ser Thr Tyr
        595                 600                 605

Arg Val Val Ser Val Leu Thr Val Leu His Gln Asp Trp Leu Asn Gly
    610                 615                 620

Lys Glu Tyr Lys Cys Lys Val Ser Asn Lys Ala Leu Pro Ala Pro Ile
625                 630                 635                 640

Glu Lys Thr Ile Ser Lys Ala Lys Gly Gln Pro Arg Glu Pro Gln Val
                645                 650                 655

Tyr Thr Leu Pro Pro Ser Arg Glu Glu Met Thr Lys Asn Gln Val Ser
            660                 665                 670

Leu Thr Cys Leu Val Lys Gly Phe Tyr Pro Ser Asp Ile Ala Val Glu
        675                 680                 685

Trp Glu Ser Asn Gly Gln Pro Glu Asn Asn Tyr Lys Thr Thr Pro Pro
    690                 695                 700

Val Leu Asp Ser Asp Gly Ser Phe Phe Leu Tyr Ser Lys Leu Thr Val
705                 710                 715                 720

Asp Lys Ser Arg Trp Gln Gln Gly Asn Val Phe Ser Cys Ser Val Met
                725                 730                 735

His Glu Ala Leu His Asn His Tyr Thr Gln Lys Ser Leu Ser Leu Ser
            740                 745                 750

Pro Gly Lys
        755


<210> SEQ ID NO 3
<211> LENGTH: 908
<212> TYPE: PRT
<213> ORGANISM: Artificial Sequence
<220> FEATURE:
<223> OTHER INFORMATION: Recombinant Spike Protein

<400> SEQUENCE: 3

Val Asn Leu Thr Thr Arg Thr Gln Leu Pro Pro Ala Tyr Thr Asn Ser
1               5                   10                  15

Phe Thr Arg Gly Val Tyr Tyr Pro Asp Lys Val Phe Arg Ser Ser Val
            20                  25                  30

Leu His Ser Thr Gln Asp Leu Phe Leu Pro Phe Phe Ser Asn Val Thr
        35                  40                  45

Trp Phe His Ala Ile His Val Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
```

-continued

```
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
    290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
        515                 520                 525

Asn Gly Leu Thr Gly Thr Gly Val Leu Thr Glu Ser Asn Lys Lys Phe
    530                 535                 540

Leu Pro Phe Gln Gln Phe Gly Arg Asp Ile Ala Asp Thr Thr Asp Ala
545                 550                 555                 560
```

-continued

Val Arg Asp Pro Gln Thr Leu Glu Ile Leu Asp Ile Thr Pro Cys Ser
565 570 575

Phe Gly Gly Val Ser Val Ile Thr Pro Gly Thr Asn Thr Ser Asn Gln
580 585 590

Val Ala Val Leu Tyr Gln Asp Val Asn Cys Thr Glu Val Pro Val Ala
595 600 605

Ile His Ala Asp Gln Leu Thr Pro Thr Trp Arg Val Tyr Ser Thr Gly
610 615 620

Ser Asn Val Phe Gln Thr Arg Ala Gly Cys Leu Ile Gly Ala Glu His
625 630 635 640

Val Asn Asn Ser Tyr Glu Cys Asp Ile Pro Ile Gly Ala Gly Ile Cys
645 650 655

Ala Ser Tyr Gln Thr Gln Thr Asn Ser Pro Arg Arg Ala Arg Gly Gly
660 665 670

Ser Gly Gly Ser Gly Gly Ser Gly Gly Ser Gly Gly Ser Thr Cys Pro
675 680 685

Pro Cys Pro Ala Pro Glu Leu Leu Gly Gly Pro Ser Val Phe Leu Phe
690 695 700

Pro Pro Lys Pro Lys Asp Thr Leu Met Ile Ser Arg Thr Pro Glu Val
705 710 715 720

Thr Cys Val Val Val Asp Val Ser His Glu Asp Pro Glu Val Lys Phe
725 730 735

Asn Trp Tyr Val Asp Gly Val Glu Val His Asn Ala Lys Thr Lys Pro
740 745 750

Arg Glu Glu Gln Tyr Asn Ser Thr Tyr Arg Val Val Ser Val Leu Thr
755 760 765

Val Leu His Gln Asp Trp Leu Asn Gly Lys Glu Tyr Lys Cys Lys Val
770 775 780

Ser Asn Lys Ala Leu Pro Ala Pro Ile Glu Lys Thr Ile Ser Lys Ala
785 790 795 800

Lys Gly Gln Pro Arg Glu Pro Gln Val Tyr Thr Leu Pro Pro Ser Arg
805 810 815

Glu Glu Met Thr Lys Asn Gln Val Ser Leu Thr Cys Leu Val Lys Gly
820 825 830

Phe Tyr Pro Ser Asp Ile Ala Val Glu Trp Glu Ser Asn Gly Gln Pro
835 840 845

Glu Asn Asn Tyr Lys Thr Thr Pro Pro Val Leu Asp Ser Asp Gly Ser
850 855 860

Phe Phe Leu Tyr Ser Lys Leu Thr Val Asp Lys Ser Arg Trp Gln Gln
865 870 875 880

Gly Asn Val Phe Ser Cys Ser Val Met His Glu Ala Leu His Asn His
885 890 895

Tyr Thr Gln Lys Ser Leu Ser Leu Ser Pro Gly Lys
900 905

<210> SEQ ID NO 4
<211> LENGTH: 1436
<212> TYPE: PRT
<213> ORGANISM: Artificial Sequence
<220> FEATURE:
<223> OTHER INFORMATION: Recombinant Spike Protein

<400> SEQUENCE: 4

Val Asn Leu Thr Thr Arg Thr Gln Leu Pro Pro Ala Tyr Thr Asn Ser
1 5 10 15

-continued

Phe Thr Arg Gly Val Tyr Tyr Pro Asp Lys Val Phe Arg Ser Ser Val
20 25 30

Leu His Ser Thr Gln Asp Leu Phe Leu Pro Phe Phe Ser Asn Val Thr
35 40 45

Trp Phe His Ala Ile His Val Ser Gly Thr Asn Gly Thr Lys Arg Phe
50 55 60

Asp Asn Pro Val Leu Pro Phe Asn Asp Gly Val Tyr Phe Ala Ser Thr
65 70 75 80

Glu Lys Ser Asn Ile Ile Arg Gly Trp Ile Phe Gly Thr Thr Leu Asp
85 90 95

Ser Lys Thr Gln Ser Leu Leu Ile Val Asn Asn Ala Thr Asn Val Val
100 105 110

Ile Lys Val Cys Glu Phe Gln Phe Cys Asn Asp Pro Phe Leu Gly Val
115 120 125

Tyr Tyr His Lys Asn Asn Lys Ser Trp Met Glu Ser Glu Phe Arg Val
130 135 140

Tyr Ser Ser Ala Asn Asn Cys Thr Phe Glu Tyr Val Ser Gln Pro Phe
145 150 155 160

Leu Met Asp Leu Glu Gly Lys Gln Gly Asn Phe Lys Asn Leu Arg Glu
165 170 175

Phe Val Phe Lys Asn Ile Asp Gly Tyr Phe Lys Ile Tyr Ser Lys His
180 185 190

Thr Pro Ile Asn Leu Val Arg Asp Leu Pro Gln Gly Phe Ser Ala Leu
195 200 205

Glu Pro Leu Val Asp Leu Pro Ile Gly Ile Asn Ile Thr Arg Phe Gln
210 215 220

Thr Leu Leu Ala Leu His Arg Ser Tyr Leu Thr Pro Gly Asp Ser Ser
225 230 235 240

Ser Gly Trp Thr Ala Gly Ala Ala Ala Tyr Tyr Val Gly Tyr Leu Gln
245 250 255

Pro Arg Thr Phe Leu Leu Lys Tyr Asn Glu Asn Gly Thr Ile Thr Asp
260 265 270

Ala Val Asp Cys Ala Leu Asp Pro Leu Ser Glu Thr Lys Cys Thr Leu
275 280 285

Lys Ser Phe Thr Val Glu Lys Gly Ile Tyr Gln Thr Ser Asn Phe Arg
290 295 300

Val Gln Pro Thr Glu Ser Ile Val Arg Phe Pro Asn Ile Thr Asn Leu
305 310 315 320

Cys Pro Phe Gly Glu Val Phe Asn Ala Thr Arg Phe Ala Ser Val Tyr
325 330 335

Ala Trp Asn Arg Lys Arg Ile Ser Asn Cys Val Ala Asp Tyr Ser Val
340 345 350

Leu Tyr Asn Ser Ala Ser Phe Ser Thr Phe Lys Cys Tyr Gly Val Ser
355 360 365

Pro Thr Lys Leu Asn Asp Leu Cys Phe Thr Asn Val Tyr Ala Asp Ser
370 375 380

Phe Val Ile Arg Gly Asp Glu Val Arg Gln Ile Ala Pro Gly Gln Thr
385 390 395 400

Gly Lys Ile Ala Asp Tyr Asn Tyr Lys Leu Pro Asp Asp Phe Thr Gly
405 410 415

Cys Val Ile Ala Trp Asn Ser Asn Asn Leu Asp Ser Lys Val Gly Gly
420 425 430

-continued

```
Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
        515                 520                 525

Asn Gly Leu Thr Gly Thr Gly Val Leu Thr Glu Ser Asn Lys Lys Phe
    530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
                565                 570                 575

Phe Gly Gly Val Ser Val Ile Thr Pro Gly Thr Asn Thr Ser Asn Gln
            580                 585                 590

Val Ala Val Leu Tyr Gln Asp Val Asn Cys Thr Glu Val Pro Val Ala
        595                 600                 605

Ile His Ala Asp Gln Leu Thr Pro Thr Trp Arg Val Tyr Ser Thr Gly
    610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser Pro Arg Arg Ala Arg Ser Val
            660                 665                 670

Ala Ser Gln Ser Ile Ile Ala Tyr Thr Met Ser Leu Gly Ala Glu Asn
        675                 680                 685

Ser Val Ala Tyr Ser Asn Asn Ser Ile Ala Ile Pro Thr Asn Phe Thr
    690                 695                 700

Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
                725                 730                 735

Leu Leu Leu Gln Tyr Gly Ser Phe Cys Thr Gln Leu Asn Arg Ala Leu
            740                 745                 750

Thr Gly Ile Ala Val Glu Gln Asp Lys Asn Thr Gln Glu Val Phe Ala
        755                 760                 765

Gln Val Lys Gln Ile Tyr Lys Thr Pro Pro Ile Lys Asp Phe Gly Gly
    770                 775                 780

Phe Asn Phe Ser Gln Ile Leu Pro Asp Pro Ser Lys Pro Ser Lys Arg
785                 790                 795                 800

Ser Phe Ile Glu Asp Leu Leu Phe Asn Lys Val Thr Leu Ala Asp Ala
                805                 810                 815

Gly Phe Ile Lys Gln Tyr Gly Asp Cys Leu Gly Asp Ile Ala Ala Arg
            820                 825                 830

Asp Leu Ile Cys Ala Gln Lys Phe Asn Gly Leu Thr Val Leu Pro Pro
        835                 840                 845

Leu Leu Thr Asp Glu Met Ile Ala Gln Tyr Thr Ser Ala Leu Leu Ala
```

-continued

```
    850                 855                 860

Gly Thr Ile Thr Ser Gly Trp Thr Phe Gly Ala Gly Ala Ala Leu Gln
865                 870                 875                 880

Ile Pro Phe Ala Met Gln Met Ala Tyr Arg Phe Asn Gly Ile Gly Val
                885                 890                 895

Thr Gln Asn Val Leu Tyr Glu Asn Gln Lys Leu Ile Ala Asn Gln Phe
            900                 905                 910

Asn Ser Ala Ile Gly Lys Ile Gln Asp Ser Leu Ser Ser Thr Ala Ser
        915                 920                 925

Ala Leu Gly Lys Leu Gln Asp Val Val Asn Gln Asn Ala Gln Ala Leu
    930                 935                 940

Asn Thr Leu Val Lys Gln Leu Ser Ser Asn Phe Gly Ala Ile Ser Ser
945                 950                 955                 960

Val Leu Asn Asp Ile Leu Ser Arg Leu Asp Lys Val Glu Ala Glu Val
                965                 970                 975

Gln Ile Asp Arg Leu Ile Thr Gly Arg Leu Gln Ser Leu Gln Thr Tyr
            980                 985                 990

Val Thr Gln Gln Leu Ile Arg Ala  Ala Glu Ile Arg Ala  Ser Ala Asn
        995                 1000                 1005

Leu Ala  Ala Thr Lys Met Ser  Glu Cys Val Leu Gly  Gln Ser Lys
    1010                 1015                 1020

Arg Val  Asp Phe Cys Gly Lys  Gly Tyr His Leu Met  Ser Phe Pro
    1025                 1030                 1035

Gln Ser  Ala Pro His Gly Val  Val Phe Leu His Val  Thr Tyr Val
    1040                 1045                 1050

Pro Ala  Gln Glu Lys Asn Phe  Thr Thr Ala Pro Ala  Ile Cys His
    1055                 1060                 1065

Asp Gly  Lys Ala His Phe Pro  Arg Glu Gly Val Phe  Val Ser Asn
    1070                 1075                 1080

Gly Thr  His Trp Phe Val Thr  Gln Arg Asn Phe Tyr  Glu Pro Gln
    1085                 1090                 1095

Ile Ile  Thr Thr Asp Asn Thr  Phe Val Ser Gly Asn  Cys Asp Val
    1100                 1105                 1110

Val Ile  Gly Ile Val Asn Asn  Thr Val Tyr Asp Pro  Leu Gln Pro
    1115                 1120                 1125

Glu Leu  Asp Ser Phe Lys Glu  Glu Leu Asp Lys Tyr  Phe Lys Asn
    1130                 1135                 1140

His Thr  Ser Pro Asp Val Asp  Leu Gly Asp Ile Ser  Gly Ile Asn
    1145                 1150                 1155

Ala Ser  Val Val Asn Ile Gln  Lys Glu Ile Asp Arg  Leu Asn Glu
    1160                 1165                 1170

Val Ala  Lys Asn Leu Asn Glu  Ser Leu Ile Asp Leu  Gln Glu Leu
    1175                 1180                 1185

Gly Lys  Tyr Glu Gln Tyr Ile  Lys Trp Pro Gly Gly  Ser Gly Gly
    1190                 1195                 1200

Ser Gly  Gly Ser Gly Gly Ser  Gly Gly Ser Thr Cys  Pro Pro Cys
    1205                 1210                 1215

Pro Ala  Pro Glu Leu Leu Gly  Gly Pro Ser Val Phe  Leu Phe Pro
    1220                 1225                 1230

Pro Lys  Pro Lys Asp Thr Leu  Met Ile Ser Arg Thr  Pro Glu Val
    1235                 1240                 1245

Thr Cys  Val Val Val Asp Val  Ser His Glu Asp Pro  Glu Val Lys
    1250                 1255                 1260
```

```
Phe Asn  Trp Tyr Val Asp Gly  Val Glu Val His Asn  Ala Lys Thr
    1265                 1270                 1275

Lys Pro  Arg Glu Glu Gln Tyr  Asn Ser Thr Tyr Arg  Val Val Ser
    1280                 1285                 1290

Val Leu  Thr Val Leu His Gln  Asp Trp Leu Asn Gly  Lys Glu Tyr
    1295                 1300                 1305

Lys Cys  Lys Val Ser Asn Lys  Ala Leu Pro Ala Pro  Ile Glu Lys
    1310                 1315                 1320

Thr Ile  Ser Lys Ala Lys Gly  Gln Pro Arg Glu Pro  Gln Val Tyr
    1325                 1330                 1335

Thr Leu  Pro Pro Ser Arg Glu  Glu Met Thr Lys Asn  Gln Val Ser
    1340                 1345                 1350

Leu Thr  Cys Leu Val Lys Gly  Phe Tyr Pro Ser Asp  Ile Ala Val
    1355                 1360                 1365

Glu Trp  Glu Ser Asn Gly Gln  Pro Glu Asn Asn Tyr  Lys Thr Thr
    1370                 1375                 1380

Pro Pro  Val Leu Asp Ser Asp  Gly Ser Phe Phe Leu  Tyr Ser Lys
    1385                 1390                 1395

Leu Thr  Val Asp Lys Ser Arg  Trp Gln Gln Gly Asn  Val Phe Ser
    1400                 1405                 1410

Cys Ser  Val Met His Glu Ala  Leu His Asn His Tyr  Thr Gln Lys
    1415                 1420                 1425

Ser Leu  Ser Leu Ser Pro Gly  Lys
    1430                 1435
```

```
<210> SEQ ID NO 5
<211> LENGTH: 40
<212> TYPE: PRT
<213> ORGANISM: Artificial Sequence
<220> FEATURE:
<223> OTHER INFORMATION: Signal Peptide

<400> SEQUENCE: 5

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Ala Asp
        35                  40
```

```
<210> SEQ ID NO 6
<211> LENGTH: 1982
<212> TYPE: DNA
<213> ORGANISM: Artificial Sequence
<220> FEATURE:
<223> OTHER INFORMATION: Recombinant Spike Protein

<400> SEQUENCE: 6

aaaattttta ctgttttcgt aacagttttg taataaaaaa acctataaat attccggatt     60

attcataccg tcccaccatc gggcgcggat cccggtccga agcgcgcgga attcatgctg    120

ctggtcaacc agagccacca gggtttcaac aaggaacaca cctcaaagat ggtgtccgcc    180

atcgtgctgt acgtcctgct ggctgctgct gctcactcag ctttcgctgc cgacaacatc    240

accaacctgt gcccattcgg cgaggtcttc aacgctacta ggttcgcctc cgtgtacgct    300

tggaaccgca agcgtatcag caactgcgtg gccgactact ctgtcctgta caactccgct    360

agcttctcta ctttcaagtg ctacggagtg tcacctacca agctgaacga cctgtgcttc    420
```

actaacgtgt acgccgactc cttcgtcatc cgcggtgacg aagtgcgtca gatcgcccca 480
ggacagaccg gcaagatcgc tgactacaac tacaagctgc ctgacgactt cactggatgc 540
gtcatcgctt ggaacagcaa caacctggac tctaaagtgg gtggcaacta caactacctg 600
tacaggctgt tcagaaagag caacctgaag cctttcgaga gggacatcag caccgaaatc 660
taccaggccg gttctactcc ctgcaacggc gtcgaaggat tcaactgcta cttccccctg 720
cagtcttacg gcttccagcc aaccaacggt gtgggctacc agccttacag agtggtcgtg 780
ctgagcttcg aactcctcca cgctccagct actgtctgcg gtcctaagaa gtctactaac 840
ctggtgaaga acaagtgcgt caacttcaac ttcaacggtc tgactggaac tggaggtggc 900
tccggaggta gcggcggatc tggtggctca ggaggttcta cttgccctcc ctgcccagct 960
cctgagctgc tgggcggacc ctccgtgttc ctgttcccac ctaagccaaa ggacactctg 1020
atgatctcac gcacccccga agtcacttgc gtcgtggtcg acgtgtccca cgaggaccca 1080
gaagtcaagt tcaactggta cgtggacggc gtggaggtcc acaacgctaa gaccaagccc 1140
agggaggaac agtacaactc aacctacaga gtggtctccg tgctgactgt cctgcaccag 1200
gactggctga acggcaagga gtacaagtgc aaggtcagca acaaggctct gcccgcccca 1260
atcgagaaga ccatctctaa ggccaaggga cagcctcgcg aaccccaggt gtacactctg 1320
cccccaagcc gtgaggaaat gaccaagaac caggtctctc tgacttgcct ggtgaaggga 1380
ttctaccctt cagacatcgc tgtggagtgg gaatccaacg gtcagcccga aaacaactac 1440
aagaccactc ctcccgtcct ggacagcgac ggctctttct tcctgtactc aaagctgacc 1500
gtggacaagt cccgttggca gcagggaaac gtgttctcat gctccgtcat gcacgaggct 1560
ctgcacaacc actacactca gaagagcctg tctctgtcac ctggcaagta actcgaggca 1620
tgcggtacca agcttgtcga gaagtactag aggatcataa tcagccatac cacatttgta 1680
gaggttttac ttgctttaaa aaacctccca cacctccccc tgaacctgaa acataaaatg 1740
aatgcaattg ttgttgttaa cttgtttatt gcagcttata atggttacaa ataaagcaat 1800
agcatcacaa atttcacaaa taaagcattt ttttcactgc atctagtgta ttgtcaaact 1860
catcatgtat ctatcatgtc tgatctgatc actgccttga gcttagagat ccgaccgata 1920
tggatctaag tccactattt gtcattttac ttcggatagc tacgaacgct acaccagctg 1980
ca 1982

<210> SEQ ID NO 7
<211> LENGTH: 2784
<212> TYPE: DNA
<213> ORGANISM: Artificial Sequence
<220> FEATURE:
<223> OTHER INFORMATION: Recombinant Spike Protein

<400> SEQUENCE: 7
aagatttact gttttcgtaa cagttttgta ataaaaaaac ctataaatat tccggattat 60
tcataccgtc ccaccatcgg gcgcggatcc cggtccgaag cgcgcggaat tcatgctgct 120
ggtgaaccag tcacaccagg gcttcaacaa ggagcacacc tcaaagatgg tctccgctat 180
cgtcctgtac gtgctgctgg ctgctgctgc tcactccgcc ttcgctgccg acatgagcct 240
gggagctgag aactctgtgg cctactcaaa caactccatc gccatcccca ccaacttcac 300
tatcagcgtc accactgaaa tcctgccagt gagcatgacc aagacttctg tcgactgcac 360
catgtacatc tgcggagaca gcactgagtg ctctaacctg ctgctgcagt acggttcttt 420

-continued

```
ctgcacccag ctgaaccgcg ctctgactgg catcgccgtg gagcaggaca agaacaccca    480
ggaagtcttc gctcaggtga agcagatcta caagactcct cccatcaagg acttcggtgg    540
cttcaacttc tcccagatcc tgcctgaccc cagcaagcca tctaagaggt cattcatcga    600
ggacctgctg ttcaacaagg tgaccctggc tgacgccggc ttcatcaagc agtacggaga    660
ctgcctgggt gacatcgctg ccagagacct gatctgcgct cagaagttca acggactgac    720
cgtcctgcca cctctgctga ctgacgaaat gatcgctcag tacacctctg ctctgctggc    780
tggtaccatc acttctggct ggactttcgg agctggtgct gccctgcaga tccctttcgc    840
tatgcagatg gcctaccgtt tcaacggcat cggagtcact cagaacgtgc tgtacgagaa    900
ccagaagctg atcgctaacc agttcaacag cgccatcgga aagatccagg actcactgtc    960
cagcactgct tctgctctgg gcaagctgca ggacgtggtc aaccagaacg ctcaggccct   1020
gaacactctg gtgaagcaac tgtcttcaaa cttcggagct atctccagcg tcctgaacga   1080
catcctgtcc cgcctggaca aggtcgaggc cgaagtgcag atcgaccgcc tgatcaccgg   1140
tcgtctgcag tcactgcaga cctacgtgac tcagcagctg atcagggctg ccgagatcag   1200
agcttccgcc aacctggctg ccactaagat gtcagaatgc gtgctgggac agtccaagcg   1260
tgtcgacttc tgcggcaagg gctaccacct gatgtcattc ccccagtccg ctccacacgg   1320
tgtggtcttc ctgcacgtca cctacgtgcc agcccaggaa aagaacttca ccactgctcc   1380
tgccatctgc cacgacggca aggctcactt cccccgcgag ggagtcttcg tgagcaacgg   1440
tacccactgg ttcgtgactc agcgtaactt ctacgaacca cagatcatca ccactgacaa   1500
caccttcgtc tctggcaact gcgacgtggt catcggaatc gtcaacaaca ctgtgtacga   1560
ccctctgcag cccgagctgg acagcttcaa ggaggaactg gacaagtact tcaagaacca   1620
cacctctcct gacgtggacc tgggcgacat ctcaggaatc aacgcttccg tggtcaacat   1680
ccagaaggag atcgacaggc tgaacgaagt cgccaagaac ctgaacgaat cactgatcga   1740
cctgcaggag ctgggcaagt acgaacagta catcaagtgg cccggaggtt ccggcggaag   1800
cggtggctct ggaggttcag gcggatccac ctgccctcct tgcccagctc ctgaactgct   1860
gggtggccct tccgtgttcc tgttccctcc caagcccaag gacactctga tgatcagcag   1920
aaccccagaa gtgacttgcg tggtcgtgga cgtctctcac gaggaccctg aagtcaagtt   1980
caactggtac gtggacggcg tcgaagtgca caacgctaag accaagcccc gcgaggaaca   2040
gtacaacagc acctaccgtg tcgtgtctgt cctgactgtg ctgcaccagg actggctgaa   2100
cggcaaggag tacaagtgca aggtgtcaaa caaggctctg cccgccccaa tcgagaagac   2160
catctccaag gccaagggcc agccaaggga acctcaggtc tacactctgc caccttcaag   2220
agaggaaatg accaagaacc aggtctccct gacttgcctg gtgaagggct tctacccttc   2280
agacatcgct gtggagtggg aatccaacgg acagcccgag aacaactaca agaccactcc   2340
cccagtgctg gacagcgacg gttctttctt cctgtacagc aagctgaccg tcgacaagtc   2400
taggtggcag cagggcaacg tcttctcttg ctcagtgatg cacgaagctc tgcacaacca   2460
ctacactcag aagtccctga gcctgtctcc tggcaagtaa ctcgaggcat gcggtaccaa   2520
gcttgtcgag aagtactaga ggatcataat cagccatacc acatttgtag aggttttact   2580
tgctttaaaa acctcccaca cctcccctga acctgaaaca taaatgatgc atgtgtggta   2640
ctgtatgcag ctatatgtac attagcatag catcacaatt cacaataagg catttttcca   2700
tgcattccag tgtgatggtc cagctcatca tgtactatca gttgatcaga tcatgctgac   2760
ctagaatccg aaccgatagt gatc                                          2784
```

<210> SEQ ID NO 8
<211> LENGTH: 3636
<212> TYPE: DNA
<213> ORGANISM: Artificial Sequence
<220> FEATURE:
<223> OTHER INFORMATION: Recombinant Spike Protein

<400> SEQUENCE: 8

```
aagaaattta ctgttttcgt aacagttttg taataaaaaa acctataaat attccggatt     60
attcataccg tcccaccatc gggcgcggat cccggtccga agcgcgcgga attcatgctg    120
ctggtcaacc agagccacca gggattcaac aaggagcaca cttccaagat ggtgagcgct    180
atcgtgctgt acgtcctgct cgctgctgct gctcactctg ctttcgctgc tgacgtcaac    240
ctcaccacta ggacccagct gcctcccgct tacaccaact cattcactag gggtgtgtac    300
taccctgaca aggtgttcag atccagcgtc ctgcactcca ctcaggacct gttcctgccc    360
ttcttcagca acgtcacctg gttccacgct atccacgtgt ccggcaccaa cggaactaag    420
aggttcgaca acccagtcct gcctttcaac gacggcgtgt acttcgcctc taccgagaag    480
tcaaacatca tcagaggttg gatcttcggc accactctgg actccaagac tcagagcctg    540
ctgatcgtca acaacgctac caacgtggtc atcaaggtgt gcgagttcca gttctgcaac    600 gacccctttcc tgggagtcta ctaccacaag aacaacaagt cttggatgga gtcagagttc    660
cgcgtctact cttcagccaa caactgcact ttcgagtacg tgtctcagcc cttcctgatg    720
gacctggaag gcaagcaggg caacttcaag aacctgcgcg agttcgtgtt caagaacatc    780
gacggttact tcaagatcta ctccaagcac accctatca acctggtccg tgacctgccc    840
cagggtttca gcgctctgga gcctctggtg gacctgccca tcggcatcaa catcacccgc    900
ttccagactc tgctggctct gcaccgttcc tacctgactc caggcgactc cagctctgga    960
tggactgctg gtgctgctgc ttactacgtg ggctacctgc agcctaggac cttcctgctg   1020
aagtacaacg aaaacggaac catcacagac gctgtggact gcgctctgga cccactgtcc   1080
gaaaccaagt gcactctgaa gagcttcacc gtggagaagg gcatctacca gacttctaac   1140
ttcagggtcc agccaaccga atcaatcgtg agattcccca acatcactaa cctgtgccca   1200
ttcggagagg tcttcaacgc cacccgtttc gcttccgtgt acgcctggaa caggaagaga   1260
atctctaact gcgtggctga ctactcagtc ctgtacaact cagcctcctt cagcaccttc   1320
aagtgctacg gtgtgtctcc tactaagctg aacgacctgt gcttcaccaa cgtgtacgct   1380
gactcattcg tcatcagggg cgacgaggtg agacagatcg ctcccggaca gactggcaag   1440
atcgccgact acaactacaa gctgccagac gacttcaccg gttgcgtcat cgcctggaac   1500
tccaacaacc tggacagcaa agtgggtggc aactacaact acctgtaccg cctgttccgt   1560
aagtccaacc tgaagccatt cgagagggac atctctactg aaatctacca ggctggctca   1620 acccccttgca acggcgtcga gggattcaac tgctacttcc cactgcagag ctacggattc   1680
cagcctacta acggcgtggg ataccagccc tacagagtgg tcgtgctgtc cttcgaactg   1740
ctgcacgccc cagctactgt gtgcggacct aagaagagca ccaacctggt gaagaacaag   1800
tgcgtcaact tcaacttcaa cggtctgacc ggtactggcg tcctgaccga gtctaacaag   1860
aagttcctgc cattccagca gttcggtcgc gacatcgctg acactaccga cgccgtgcgt   1920
gacccacaga ccctggaaat cctggacatc actccatgct ctttcggagg tgtgtcagtc   1980
atcactcctg gcaccaacac ttcaaaccag gtggccgtcc tgtaccagga cgtcaactgc   2040
```

-continued

```
accgaggtgc ctgtcgccat ccacgctgac cagctgaccc ccacttggcg cgtctactca   2100

accggttcca acgtgttcca gactcgtgct ggctgcctga tcggagccga gcacgtgaac   2160

aactcctacg aatgcgacat ccccatcgga gctggtatct gcgcctccta ccagacccaa   2220

actaacagcc cacgcagggc tcgcggcgga agcggtggct ctggaggttc aggcggatcc   2280

ggtggcagca cttgcccacc ttgcccagct ccagaactgc tgggaggtcc aagcgtgttc   2340

ctgttccctc ctaagcctaa ggacaccctg atgatctccc gtacccctga ggtcacttgc   2400

gtcgtggtcg acgtgagcca cgaggacccc gaagtcaagt tcaactggta cgtggacggc   2460

gtggaagtcc acaacgctaa gaccaagccc cgcgaggaac agtacaactc cacttaccgt   2520

gtggtcagcg tgctgaccgt cctgcaccag gactggctga acggaaagga atacaagtgc   2580

aaggtctcta acaaggccct gcctgctccc atcgaaaaga ctatctcaaa ggctaagggt   2640

cagcccaggg agccacaggt gtacaccctg cctccctcta gagaggaaat gaccaagaac   2700

caggtctcac tgacttgcct ggtgaaggga ttctacccat ccgacatcgc cgtggagtgg   2760

gaaagcaacg gtcagcctga gaacaactac aagaccactc cacctgtcct ggactctgac   2820

ggttcattct tcctgtactc taagctgact gtggacaagt cacgttggca gcagggcaac   2880

gtgttctctt gctcagtcat gcacgaagct ctgcacaacc actacaccca gaagtccctg   2940

agcctgtctc ctggcaagta actcgaggca tgcggtacca agcttgtcga gaagtactag   3000

aggatcataa tcagccatac cacatttgta gaggttttac ttgctttaaa aaacctccca   3060

cacctccccc tgaacctgaa acataaaatg aatgcaattg ttgttgttaa cttgtttatt   3120

gcagcttata atggttacaa ataaagcaat agcatcacaa atttcacaaa taaagcattt   3180

ttttcactgc attctagttg tggtttgtcc aaactcatca atgtatctta tcatgtctgg   3240

atctgatcac tgcttgagcc taggagatcc gaaccagata agtgaaatct agttccaaac   3300

tattttgtca tttttaattt tcgtattagc ttacgacgct acacccagta cccatctatt   3360

ttgtcactct tccctaaata atccttaaaa actccatttc cacccctccc agttcccaac   3420

taattttgtc cgcccacaca ggggcatttt tcttcctgtt atgtgaattc ctgcagcccg   3480

ggaggatcca ctaagttcta gagcggccgc cacgcggtgg agctccggct tttgttgccg   3540

gttactggag ggtcagttgc gcgcttagac gtatcatggg tcgtagctgt tatcgctggc   3600

gtgcacctgc acgagctatg aggaggagga gactta                             3636
```

```
<210> SEQ ID NO 9
<211> LENGTH: 4545
<212> TYPE: DNA
<213> ORGANISM: Artificial Sequence
<220> FEATURE:
<223> OTHER INFORMATION: Recombinant Spike Protein

<400> SEQUENCE: 9
```

```
aagaatttta ctgttttcgt aacagttttg taataaaaaa acctataaat attccggatt     60

attcataccg tcccaccatc gggcgcggat cccggtccga agcgcgcgga attcatgctg    120

ctggtgaacc agtcccacca gggattcaac aaggagcaca ctagcaagat ggtctctgct    180

atcgtgctgt acgtcctgct ggctgctgct gctcacagcg ccttcgctgc cgacgtgaac    240

ctcaccacta ggacccagct gcctcccgct tacaccaact ctttcactag ggtgtctac     300

tacccagaca aggtgttcag atccagcgtc ctgcacagca ctcaggacct gttcctgcct    360

ttcttctcta acgtgacctg gttccacgcc atccacgtct ccggtaccaa cggcactaag    420

cgcttcgaca acccagtcct gcctttcaac gacggcgtgt acttcgcttc aaccgaaaag    480
```

-continued

```
tccaacatca tccgtggatg gatcttcggt accactctgg acagcaagac tcagtctctg    540
ctgatcgtga acaacgccac caacgtggtc atcaaggtct gcgagttcca gttctgcaac    600
gacccccttcc tgggagtgta ctaccacaag aacaacaagt catggatgga gtccgagttc    660
cgcgtgtact cttcagctaa caactgcact ttcgagtacg tcagccagcc attcctgatg    720
gacctggaag gaaagcaggg taacttcaag aacctgaggg agttcgtgtt caagaacatc    780
gacggttact tcaagatcta cagcaagcac acccccatca acctggtgag agacctgcca    840
cagggattct ctgctctgga acccctggtc gacctgccaa tcggtatcaa catcacccgc    900
ttccagactc tgctggctct gcaccgttcc tacctgactc ctggcgactc cagctctgga    960
tggactgctg gagctgctgc ttactacgtg ggatacctgc agccaaggac cttcctgctg   1020
aagtacaacg agaacggtac catcactgac gccgtggact gcgctctgga cccactgtca   1080
gaaaccaagt gcactctgaa gtccttcacc gtcgagaagg gtatctacca gactagcaac   1140
ttcagggtcc agcctaccga atctatcgtg agattcccaa acatcactaa cctgtgccct   1200
ttcggcgagg tgttcaacgc caccagattc gcttccgtct acgcctggaa caggaagaga   1260
atcagcaact gcgtggctga ctactctgtc ctgtacaaca gcgcctcttt ctcaaccttc   1320
aagtgctacg gcgtgtcacc tactaagctg aacgacctgt gcttcaccaa cgtgtacgcc   1380
gactccttcg tcatcagggg agacgaggtg agacagatcg ctcctggcca gactggaaag   1440
atcgccgact acaactacaa gctgcccgac gacttcaccg gttgcgtgat cgcttggaac   1500
agcaacaacc tggactctaa ggtcggtggc aactacaact acctgtaccg cctgttccgt   1560
aagagcaacc tgaagccctt cgagagggac atcagcactg aaatctacca ggccggatct   1620
accccatgca acggtgtgga aggcttcaac tgctacttcc ctctgcagtc ttacggtttc   1680
cagcccacta acggtgtcgg ctaccagcca tacagagtgg tcgtgctgag cttcgagctg   1740
ctgcacgccc ctgctactgt gtgcggtccc aagaagtcta ccaacctggt gaagaacaag   1800
tgcgtcaact tcaacttcaa cggcctgacc ggaactggtg tgctgaccga atcaaacaag   1860
aagttcctgc ctttccagca gttcggccgc gacatcgctg acaccactga cgccgtccgt   1920
gacccacaga ccctggagat cctggacatc actccttgct cattcggagg tgtgtccgtc   1980
atcactcccg gaaccaacac ttccaaccag gtggctgtcc tgtaccagga cgtgaactgc   2040
actgaggtgc ctgtggctat ccacgctgac cagctgaccc caacttggcg cgtctactca   2100
accggctcca acgtgttcca gactcgtgct ggttgcctga tcggcgccga gcacgtcaac   2160
aacagctacg aatgcgacat ccctatcggc gctggaatct gcgcctctta ccagacccag   2220
actaacagcc cccgcagggc taggtctgtg gcttcccaga gcatcatcgc ttacaccatg   2280
tcactgggtg ctgaaaactc cgtcgcctac agcaacaact ctatcgccat cccaaccaac   2340
ttcactatct cagtcaccac tgagatcctg cctgtgagca tgaccaagac ttctgtcgac   2400
tgcactatgt acatctgcgg cgacagcacc gaatgctcta acctgctgct gcagtacggt   2460
tccttctgca cccagctgaa ccgtgctctg actggcatcg ccgtggagca ggacaagaac   2520
actcaggaag tgttcgctca ggtcaagcag atctacaaga ccccacctat caaggacttc   2580
ggcggattca acttctccca gatcctgcca gacccttcaa agccctccaa gcgcagcttc   2640
atcgaagacc tgctgttcaa caaggtgacc ctggccgacg ctggattcat caagcagtac   2700
ggagactgcc tgggtgacat cgccgctcgt gacctgatct gcgctcagaa gttcaacggt   2760
ctgaccgtcc tgcccccact gctgactgac gagatgatcg cccagtacac ttcagccctg   2820
```

-continued

```
ctggctggta ccatcacttc tggatggacc ttcggtgctg gtgctgctct gcagatccca   2880

ttcgctatgc agatggccta ccgtttcaac ggaatcggtg tgacccagaa cgtcctgtac   2940

gaaaaccaga agctgatcgc taaccagttc aacagcgcca tcggcaagat ccaggacagc   3000

ctgtcatcca ctgcctctgc tctgggaaag ctgcaggacg tcgtgaacca gaacgcccag   3060

gctctgaaca ccctggtgaa gcagctgagc tctaacttcg gagctatctc atccgtcctg   3120

aacgacatcc tgtctcgcct ggacaaggtg gaggccgaag tccagatcga ccgcctgatc   3180

actggtcgtc tgcagtcact gcagacctac gtgactcagc agctgatcag ggccgctgaa   3240

atcagagcct ccgctaacct ggccgctacc aagatgtcag agtgcgtgct gggacagtcc   3300

aagcgtgtcg acttctgcgg caagggatac cacctgatgt cattcccaca gtccgctcct   3360

cacggcgtcg tgttcctgca cgtgacctac gtccctgccc aggagaagaa cttcaccact   3420

gcccccgcta tctgccacga cggcaaggct cacttcccta gggaaggagt gttcgtctca   3480

aacggtaccc actggttcgt gactcagaga aacttctacg agccccagat catcaccact   3540

gacaacactt tcgtctccgg caactgcgac gtcgtgatcg gaatcgtgaa caacaccgtc   3600

tacgaccccc tgcagccaga actggactca ttcaaggagg aactggacaa gtacttcaag   3660

aaccacacct ccccagacgt ggacctgggc gacatctcag gaatcaacgc ttccgtcgtg   3720

aacatccaga aggagatcga ccgcctgaac gaagtcgcca agaacctgaa cgagagcctg   3780

atcgacctgc aggagctggg caagtacgaa cagtacatca agtggcctgg tggctctgga   3840

ggttcaggcg gatccggtgg cagcggaggt tcaacctgcc ctccctgccc tgctccagag   3900

ctgctgggcg gaccttctgt gttcctgttc ccacctaagc ccaaggacac cctgatgatc   3960

agccgtaccc cagaagtgac ttgcgtcgtg gtcgacgtct ctcacgagga ccctgaagtc   4020

aagttcaact ggtacgtgga cggcgtggag gtccacaacg ctaagaccaa gcctcgcgag   4080

gaacagtaca actcaactta ccgtgtggtc tccgtgctga ccgtcctgca ccaggactgg   4140

ctgaacggca aggagtacaa gtgcaaggtg tcaaacaagg ccctgcctgc tcccatcgaa   4200

aagactatct ccaaggccaa gggacagcct agggagcccc aggtctacac cctgccccca   4260

tcaagagagg aaatgaccaa gaaccaggtc tccctgactt gcctggtgaa gggtttctac   4320

ccctcagaca tcgctgtgga gtgggaatcc aacggccagc cagaaaacaa ctacaagacc   4380

actcctcccg tgctggactc agacggctcc ttcttcctgt acagcaagct gactgtcgac   4440

aagtctcgct ggcagcaggg aaacgtgttc tcttgctcag tcatgcacga ggctctgcac   4500

aaccactaca cccagaagtc cctgagcctg tctcccggca agtaa                   4545
```

<210> SEQ ID NO 10
<211> LENGTH: 419
<212> TYPE: PRT
<213> ORGANISM: Unknown
<220> FEATURE:
<223> OTHER INFORMATION: Coronavirus

<400> SEQUENCE: 10

```
Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60
```

```
Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala
```

<210> SEQ ID NO 11
<211> LENGTH: 75
<212> TYPE: PRT
<213> ORGANISM: Unknown
<220> FEATURE:
<223> OTHER INFORMATION: Coronavirus

<400> SEQUENCE: 11

-continued

```
Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Ser Phe Tyr Val Tyr Ser Arg Val Lys Asn
    50                  55                  60

Leu Asn Ser Ser Arg Val Pro Asp Leu Leu Val
65                  70                  75


<210> SEQ ID NO 12
<211> LENGTH: 222
<212> TYPE: PRT
<213> ORGANISM: Unknown
<220> FEATURE:
<223> OTHER INFORMATION: Coronavirus

<400> SEQUENCE: 12

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
        35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
        115                 120                 125

Leu Thr Arg Pro Leu Leu Glu Ser Glu Leu Val Ile Gly Ala Val Ile
    130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
            180                 185                 190

Phe Ala Ala Tyr Ser Arg Tyr Arg Ile Gly Asn Tyr Lys Leu Asn Thr
        195                 200                 205

Asp His Ser Ser Ser Ser Asp Asn Ile Ala Leu Leu Val Gln
    210                 215                 220
```